US011510847B2

(12) United States Patent
West et al.

(10) Patent No.: US 11,510,847 B2
(45) Date of Patent: Nov. 29, 2022

(54) SPINNING FEMALE LUER WITH THREADABLY REMOVABLE FEATURE

(71) Applicant: Becton, Dickinson and Company, Franklin Lakes, NJ (US)

(72) Inventors: Robert E. West, Basking Ridge, NJ (US); Jude Cancellieri, Oakland, NJ (US); Kivilcim Eralp, New York, NY (US); Jayeon Kim, River Edge, NJ (US); Alicia Malbin, Ridgewood, NJ (US); Girum Yemane-Tekeste, Hackensack, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 635 days.

(21) Appl. No.: 16/101,988

(22) Filed: Aug. 13, 2018

(65) Prior Publication Data
US 2019/0053980 A1 Feb. 21, 2019

Related U.S. Application Data

(60) Provisional application No. 62/545,597, filed on Aug. 15, 2017.

(51) Int. Cl.
*A61J 1/14* (2006.01)
*A61J 1/20* (2006.01)
*A61M 39/10* (2006.01)

(52) U.S. Cl.
CPC .......... *A61J 1/1418* (2015.05); *A61J 1/2048* (2015.05); *A61J 1/2055* (2015.05); *A61J 1/2096* (2013.01);
(Continued)

(58) Field of Classification Search
CPC ...... A61J 1/1418; A61J 1/2055; A61J 1/2048; A61J 1/2096; A61J 1/201; A61J 1/2065;
(Continued)

(56) References Cited

U.S. PATENT DOCUMENTS 5,462,531 A * 10/1995 Novacek ............... A61L 2/28
604/110
10,561,802 B2  2/2020 Kim et al.
(Continued)

FOREIGN PATENT DOCUMENTS

CN     106237421 A    12/2016
JP     2017515544 A    6/2017
(Continued)

*Primary Examiner* — Philip R Wiest
*Assistant Examiner* — Alessandro R Del Priore
(74) *Attorney, Agent, or Firm* — The Webb Law Firm

(57) ABSTRACT

An adapter for connection with a fluid container includes an outer housing having a distal end, a proximal end, and a substantially cylindrical sidewall extending between the distal end and the proximal end, an inner member including a body rotatably inserted within the outer housing, a connector extending from the body configured to connect the adapter to a fluid container, and at least one grasping member extending from the inner member, the grasping member being configured for grasping by a user of the adapter, a first locking arrangement engageable with a distal end of the inner member and configured to restrict the inner member from rotating relative to the outer housing in a first direction, and a second locking arrangement engageable with a proximal end of the inner member and configured to restrict the inner member from moving in a proximal direction relative to the outer housing.

29 Claims, 23 Drawing Sheets

(52) U.S. Cl.
CPC .............. *A61J 1/201* (2015.05); *A61J 1/2065* (2015.05); *A61M 39/1011* (2013.01)

(58) Field of Classification Search
CPC ........ A61J 1/20–2096; A61M 39/1011; A61M 39/10; A61M 2039/1072; A61M 2039/1077; A61M 2039/1038; A61M 5/31; A61M 5/347
See application file for complete search history.

(56) References Cited

U.S. PATENT DOCUMENTS

| | | | | |
|---|---|---|---|---|
| 2012/0168464 | A1* | 7/2012 | Koyama | A61M 5/28 222/153.06 |
| 2013/0144246 | A1 | 6/2013 | Takemoto | |
| 2014/0150925 | A1* | 6/2014 | Sjogren | A61M 5/1782 141/94 |
| 2015/0297453 | A1* | 10/2015 | Kim | A61J 1/2096 285/92 |
| 2015/0297839 | A1* | 10/2015 | Sanders | A61J 1/2096 604/241 |
| 2015/0297881 | A1* | 10/2015 | Sanders | A61M 39/1011 604/535 |
| 2016/0361504 | A1* | 12/2016 | Kim | A61M 5/347 |

FOREIGN PATENT DOCUMENTS

| | | |
|---|---|---|
| WO | 2012002316 A1 | 1/2012 |
| WO | 2016199133 A1 | 12/2016 |

\* cited by examiner

SPINNING FEMALE LUER WITH THREADABLY REMOVABLE FEATURE

CROSS-REFERENCE TO RELATED APPLICATION

The present application claims priority to U.S. Provisional Application Ser. No. 62/545,597, entitled "Spinning Female Luer with Threadably Removable Feature" filed Aug. 15, 2017, the entire disclosure of which is hereby incorporated by reference.

BACKGROUND OF THE INVENTION

Field of the Invention

The present invention relates to an adapter for a closed system transfer assembly that permits fluid delivery from a first fluid container to a second fluid container through the adapter. More specifically, the invention is directed to an adapter with a connection arrangement for engaging and disengaging the adapter from the fluid container.

Description of Related Art

Healthcare workers, such as pharmacists and nurses, can be subject to acute and long term health risks upon repeated exposure to drugs or solvents which might escape into the air during drug preparation, drug administration, and/or other similar handling. This problem is particularly serious when cytotoxins, antiviral drugs, antibiotics, and radiopharmaceuticals are used by the healthcare workers. The health risks faced by exposure to these drugs can include the development of cancer, reproductive problems, genetic conditions, and other serious health concerns. Other hazardous areas may be sample taking, such as samples concerning virus infections or similar situations. When performing infusions, it is often necessary to inject a drug or other medical substance into the infusion fluid, inside an infusion bag, or other infusion fluid container. This is often done by means of penetrating a septum or other fluid barrier of an injection port on the infusion bag or on the infusion fluid line with a needle of a syringe filled with the medical fluid in question. However, even before this situation occurs, it may be necessary to transfer the medical fluid from a vial to a syringe and then from the syringe to a secondary container. In each of these steps, staff may be exposed to the medical fluid by means of contamination. Such contamination may be vaporized medical fluid or aerosol in the air. The contamination may contaminate the staff through their lungs or by vaporized medical fluid or aerosol in the air that condensates on the skin to penetrate the skin of the staff. Some medicaments are even known to penetrate protection gloves and, thereby, contaminate the staff.

Exposure to contaminations like this may, on a long term basis, give rise to alarmingly high concentrations of medicaments in the blood or the human body of the staff as described above. It has been understood that, due to the many transferring steps between e.g., vials, syringes, infusion systems, etc., the risk for contamination during the actual insertion and retraction of a needle from the container, e.g., a vial, needs to be contained. Closed system transfer devices (CSTD) have been developed to ensure that the medicament is contained in the transfer device during transfer of the medicament.

Generally, a CSTD includes an adapter (referred to hereinafter as a syringe adapter) for connection to a first fluid container, such as a syringe, and a second adapter (referred to hereinafter as a vial adapter) for connection to a vial, a second syringe, or a conduit providing fluid access to the patient's circulatory system. According to one arrangement, the healthcare practitioner may reconstitute a powdered or lyophilized compound with saline or some other reconstitution medium by attaching the syringe to the vial through the syringe adapter and the vial adapter. The practitioner reconstitutes the drug, aspirates the compound into the syringe, disconnects the adapter, and then attaches the syringe adapter and syringe attached thereto to a patient delivery device, such as an IV line, for administration to the patient.

One type of syringe adapter that can be used in a CSTD has a proximal end with a male or female luer-lock element that is arranged to be joined with a corresponding female or male luer-lock element of the syringe. The luer-lock element can be screwed into and unscrewed from the corresponding luer-lock element. It is desirable to prevent accidental or inadvertent unscrewing of the components, which could lead to the disconnection of the fluid passageway extending through the adapter. Such disconnection may result in a serious contamination risk for a patient and/or any other person in the vicinity of the disconnected CSTD. The issue of safety in administration of hazardous medical compounds is one that has been identified as being of critical importance by professional organizations and government agencies alike.

It is, therefore, desirable to provide a syringe adapter for enabling fluid transfer from the syringe to the syringe adapter, vial adapter, and/or second fluid container, such as a line connector/adaptor, by facilitating a positive connection of the connectors and avoiding inadvertent or accidental disconnection of the syringe and the fluid connector. Specifically, it is desirable that the syringe and the syringe adapter may be connected together via a simple intuitive connection activity.

SUMMARY OF THE INVENTION

According to one aspect of the invention, an adapter for connection with a fluid container includes an outer housing having a distal end, a proximal end, and a substantially cylindrical sidewall extending between the distal end and the proximal end, an inner member including a body rotatably inserted within the outer housing, a connector extending from the body configured to connect the adapter to a fluid container, and at least one grasping member extending from the inner member, the grasping member being configured for grasping by a user of the adapter, a first locking arrangement engageable with a distal end of the inner member and configured to restrict the inner member from rotating relative to the outer housing in a first direction, and a second locking arrangement engageable with a proximal surface of the inner member and configured to restrict the inner member from moving in a proximal direction relative to the outer housing. The adapter is transitionable between a disengaged state, in which the first locking arrangement and the second locking arrangement are not engaged with the inner member, a first fully engaged state in which the first locking arrangement engages the inner member, and a second fully engaged state in which the second locking arrangement engages the inner member.

According to another aspect of the invention, the inner member is rotatable in both the first direction and the second direction when the connector is in the disengaged state. The inner member is transitionable from an extended position to a recessed position by applying a compressive force to the inner member. The first locking arrangement includes at least one tooth extending inward from an inner surface of the sidewall of the outer housing and a corresponding tooth on the body of the inner member configured to engage the tooth on the sidewall. The at least one tooth extending inward from the inner surface of the sidewall of the outer housing and the corresponding tooth on the body of the inner member include an angled portion and a vertical locking surface. The first locking arrangement includes a plurality of teeth extending around a circumferential inner surface of the sidewall of the outer housing and a plurality of corresponding teeth extending from a distal end of the body of the inner member. The second locking arrangement includes at least one inwardly extending locking tab connected to a portion of an inner surface of the sidewall of the outer housing and configured to engage the proximal surface of the inner member. The second locking arrangement includes at least two inwardly extending locking tabs positioned on opposing sides of the sidewall of the outer housing. The at least one locking tab includes a locking surface configured such that applying a compressive force to the inner member biases the tab outward to insert the inner member into the outer housing. The connector includes an outer surface with helical threads, configured to engage corresponding threads on an inner surface of a portion of the fluid container. The connector includes a luer connector configured to receive a corresponding luer connector of the fluid container. The at least one grasping member includes two curved flanges extending from a proximal surface of the inner member, each curved flange including a planar portion and an angled portion extending from each end of the planar portion. The curved flanges are configured for grasping by the user to prevent rotation of the inner member in a second direction, in which the second direction is opposite the first direction. The at least one grasping member includes two bumps extending from a proximal surface of the inner member, each bump having a substantially hemispherical shape. The bumps are configured for pressing by the user to prevent rotation of the inner member in a second direction, in which the second direction is opposite the first direction. The at least one grasping member includes two flanges positioned on the connector, each flange including a vertical portion that extends vertically along a side surface of the connector. The flanges are configured for grasping by the user to prevent rotation of the inner member in a second direction, in which the second direction is opposite the first direction. One of the flanges further includes a horizontal portion that extends horizontally from the connector and perpendicular to the vertical portion. The at least one grasping member includes a thumb stop extending horizontally from the connector and vertically from the body. The thumb stop is configured for grasping by the user to prevent rotation of the inner member in a second direction, in which the second direction is opposite the first direction. The at least one grasping member includes a groove defined in the body of the inner member. The groove is configured for grasping by the user to prevent rotation of the inner member in a second direction, in which the second direction is opposite the first direction.

In another aspect of the invention, a method of disconnecting a fluid container to an adapter includes the steps of providing an adapter; grasping the at least one grasping member; moving the fluid container in an axial direction towards the adapter; and rotating the fluid container to disconnect the fluid container from the inner member of the adapter. The adapter including an outer housing having a distal end, a proximal end, and a substantially cylindrical sidewall extending between the distal end and the proximal end, an inner member including a body rotatably inserted within the outer housing, a connector extending from the body configured to connect the adapter to a fluid container, and at least one grasping member extending from the inner member, the grasping member being configured for grasping by a user of the adapter, a first locking arrangement engageable with a distal end of the inner member and configured to restrict the inner member from rotating relative to the outer housing in a first direction, and a second locking arrangement engageable with a proximal surface of the inner member and configured to restrict the inner member from moving in a proximal direction relative to the outer housing.

In another aspect of the invention, the at least one grasping member includes two curved flanges extending from a proximal surface of the inner member, each curved flange including a planar portion and an angled portion extending from each end of the planar portion. The curved flanges are configured for grasping by the user to prevent rotation of the inner member in a second direction, in which the second direction is opposite the first direction. The at least one grasping member includes two flanges positioned on the connector, each flange including a vertical portion that extends vertically along a side surface of the connector. The flanges are configured for grasping by the user to prevent rotation of the inner member in a second direction, in which the second direction is opposite the first direction.

In another aspect of the invention, an adapter for connection with a fluid container includes an outer housing having a distal end, a proximal end, and a sidewall extending between the distal end and the proximal end, a hub cover attached to the proximal end of the outer housing, an inner member including a rotatable body inserted within the outer housing and a connector extending from the body configured to connect the adapter to a fluid container, a first locking arrangement engageable with the outer housing and configured to restrict the inner member from rotating relative to the outer housing in a first direction, and a second locking arrangement engageable with the outer housing and configured to restrict the inner member from moving in a proximal direction relative to the outer housing. The adapter is transitionable between a disengaged state, in which both the first locking arrangement and the second locking arrangement are not engaged with the inner member, a first fully engaged state in which the first locking arrangement engages the outer housing, and a second fully engaged state in which the second locking arrangement engages the outer housing.

The hub cover is integrally formed on the proximal end of the outer housing and is configured to surround the rotatable body of the inner member when the inner member is connected to the outer housing. The hub cover is substantially flexible so as to contact the inner member to prevent rotation of the inner member relative to the outer housing. The inner member is rotatable in both the first direction and the second direction when the connector is in the disengaged state, wherein the inner member is prevented from rotating in a first direction when the connector is in the first fully engaged state; and wherein the inner member is prevented from retracting proximally out of the housing while permitting the inner member to rotate freely in the second fully engaged state. The inner member is transitionable from an extended position to a recessed position by applying a compressive force to the inner member. The first locking arrangement includes at least one tooth extending inward from an inner surface of the inner member and at least one recess defined in the proximal end of the outer housing configured to engage the tooth on the inner member. The at least one tooth extending inward from the inner member and the corresponding recess defined in the outer housing include an angled portion and a vertical locking surface. The second locking arrangement includes at least one inwardly extending locking tab connected to a portion of an inner surface of the inner member and configured to engage a locking protrusion extending from the proximal end of the outer housing. The at least one locking tab includes a locking surface configured such that applying a compressive force to the inner member biases the locking tab outward to insert the inner member into the outer housing. The sidewall of the outer housing defines at least one indentation to assist a user in gripping the adapter.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

DESCRIPTION OF THE INVENTION

Figure 1:
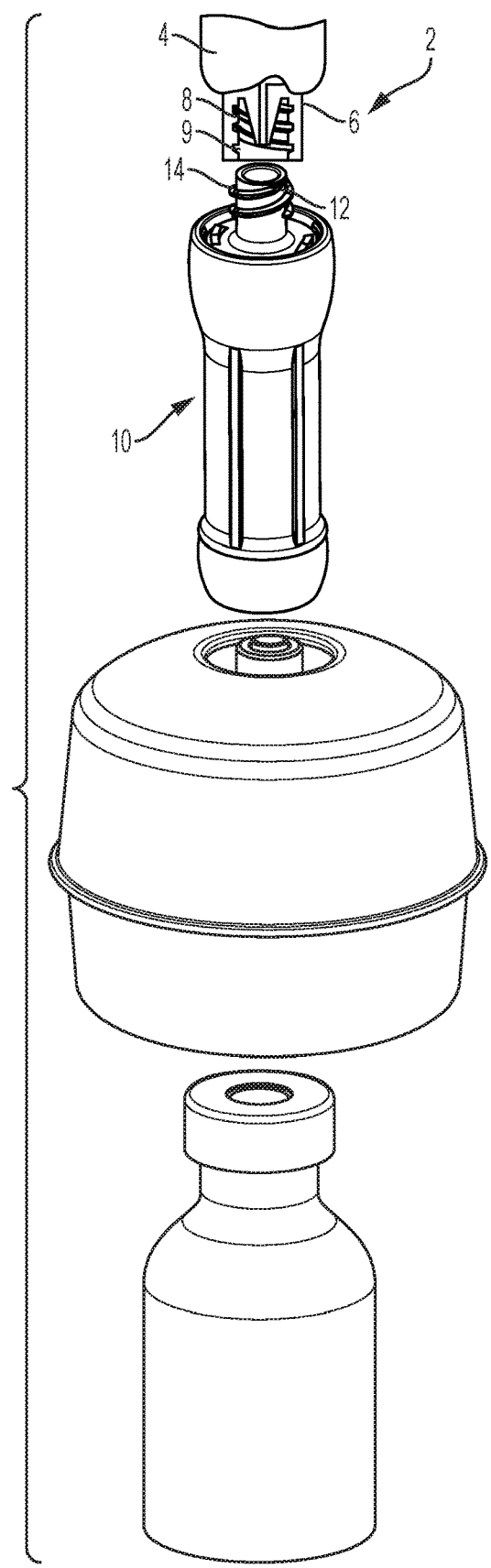
FIG. 1 is a perspective view of a closed system transfer device system according to an aspect of the invention.

The illustrations generally show preferred and non-limiting aspects of the systems and methods of the present disclosure. While the descriptions present various aspects of the devices, it should not be interpreted in any way as limiting the disclosure. Furthermore, modifications, concepts, and applications of the disclosure's aspects are to be interpreted by those skilled in the art as being encompassed by, but not limited to, the illustrations and descriptions herein.

Further, for purposes of the description hereinafter, the terms "end", "upper", "lower", "right", "left", "vertical", "horizontal", "top", "bottom", "lateral", "longitudinal", and derivatives thereof shall relate to the disclosure as it is oriented in the drawing figures. However, it is to be understood that the disclosure may assume various alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the aspects disclosed herein are not to be considered as limiting. For the purpose of facilitating understanding of the disclosure, the accompanying drawings and description illustrate preferred aspects thereof, from which the disclosure, various aspects of its structures, construction and method of operation, and many advantages may be understood and appreciated.

With reference to FIG. 1, a closed system transfer assembly 2 is illustrated. The closed system transfer assembly 2 includes a first fluid source or container, such as a syringe 4 or IV line, configured to be connected to a syringe adapter (referred to hereinafter as adapter 10). The syringe 4 includes a male luer connector 6 that is configured to be secured to a corresponding female luer-lock connector 12 of the adapter 10. However, it is understood that the arrangement of the male and female luer-lock fittings may be reversed for certain fluid delivery applications. Any other connection interface, as is known in the art, may also be added in place of the luer fittings as required. The distal end of the syringe 4 may also include a luer-lock 8 surrounding the male luer connector 6 with threads 9 configured to engage corresponding threads 14 surrounding the connector 12. More specifically, the adapter 10 is an assembly of components adapted to create a tamper-proof connection interface with the syringe 4. The adapter 10 is configured to prevent accidental or inadvertent disconnection of the adapter 10 and the syringe 4, which could compromise the integrity of the closed system transfer assembly 2. As will be described in detail hereinafter, the adapter 10 includes various locking arrangements for preventing a user from inadvertently disengaging the adapter 10 from the syringe 4. As a result of the locking arrangements, to disengage the syringe 4 from the adapter 10, the user must perform a compound motion activity. As referred to hereinafter, a compound motion activity refers to more than one distinct and independent motion performed in a predetermined order or sequence. For example, in one aspect of the adapter 10, the compound motion activity includes at least three distinct motions, namely pressing the syringe 4 toward the adapter 10, pressing a button, tab, or surface located on the adapter 10, and rotating the syringe 4 relative to the adapter 10 to disengage the threads 14 of the connector 10 from the threads 9 on the luer-lock 8 of the syringe 4. The sequence of predetermined steps may also be reversed or performed in a different order within the scope of the present invention.

With reference to FIGS. 2-8, the adapter 10 includes an outer housing 16 having a distal end 18, a proximal end 20, and a generally cylindrical sidewall 22 extending between the distal end 18 and the proximal end 20. The housing 16 defines a fluid passageway 24 (shown in FIG. 6) extending between the proximal end 20 and distal end 18 of the outer housing 16. The housing 16 may be formed from any suitable structural material including medical grade plastic or metal. Optionally, the housing 16 may include various features that make holding or manipulating the housing 16 and adapter 10 easier. For example, the housing 16 may include a narrower grip portion 26 that is more comfortable for users to hold. The housing 16 may also include a plurality of ribs 27 or a textured portion or surface (not shown) so that the housing 16 does not slip or slide when held by the user. The housing 16 may also include various aesthetic features such as patterns, designs, logos, and the like for improving the appearance of the outer housing 16.

Figure 6:
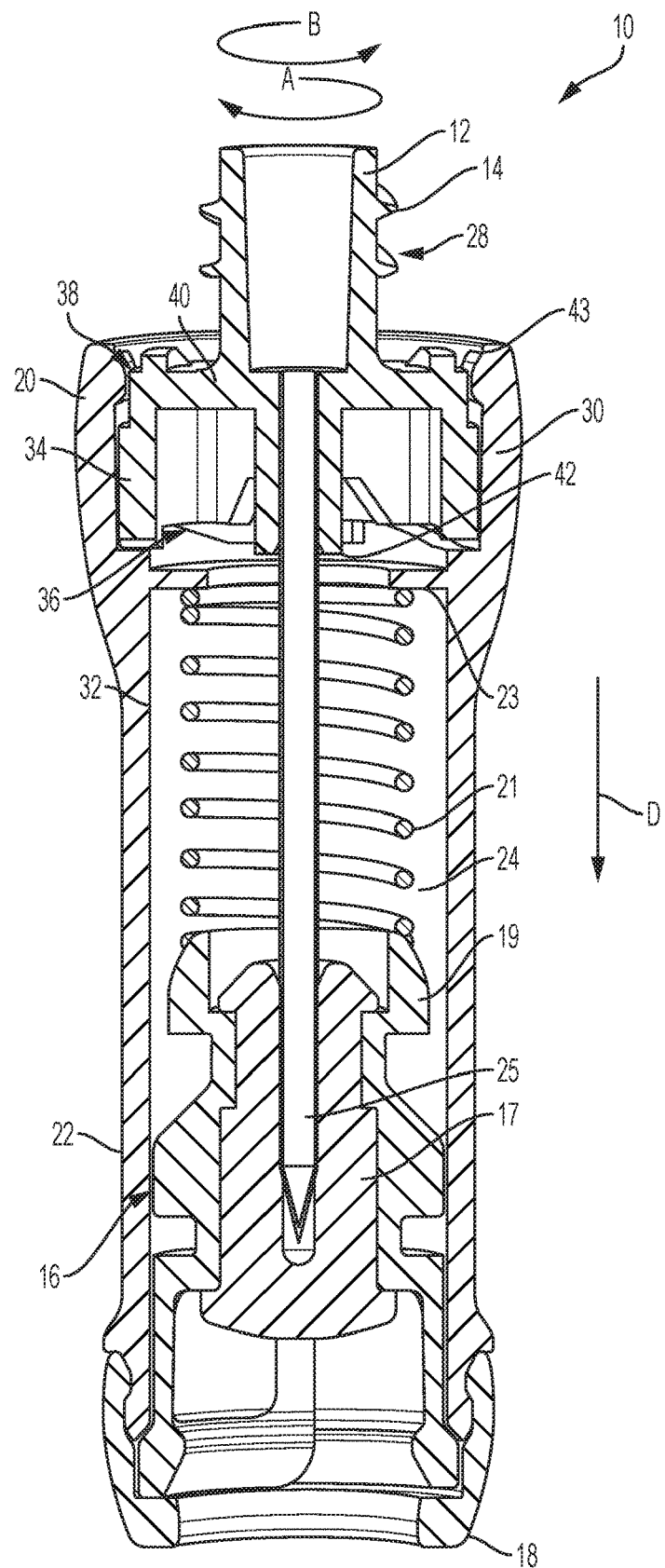
FIG. 6 is a cross-sectional view of the adapter of FIG. 2.
Figure 7:
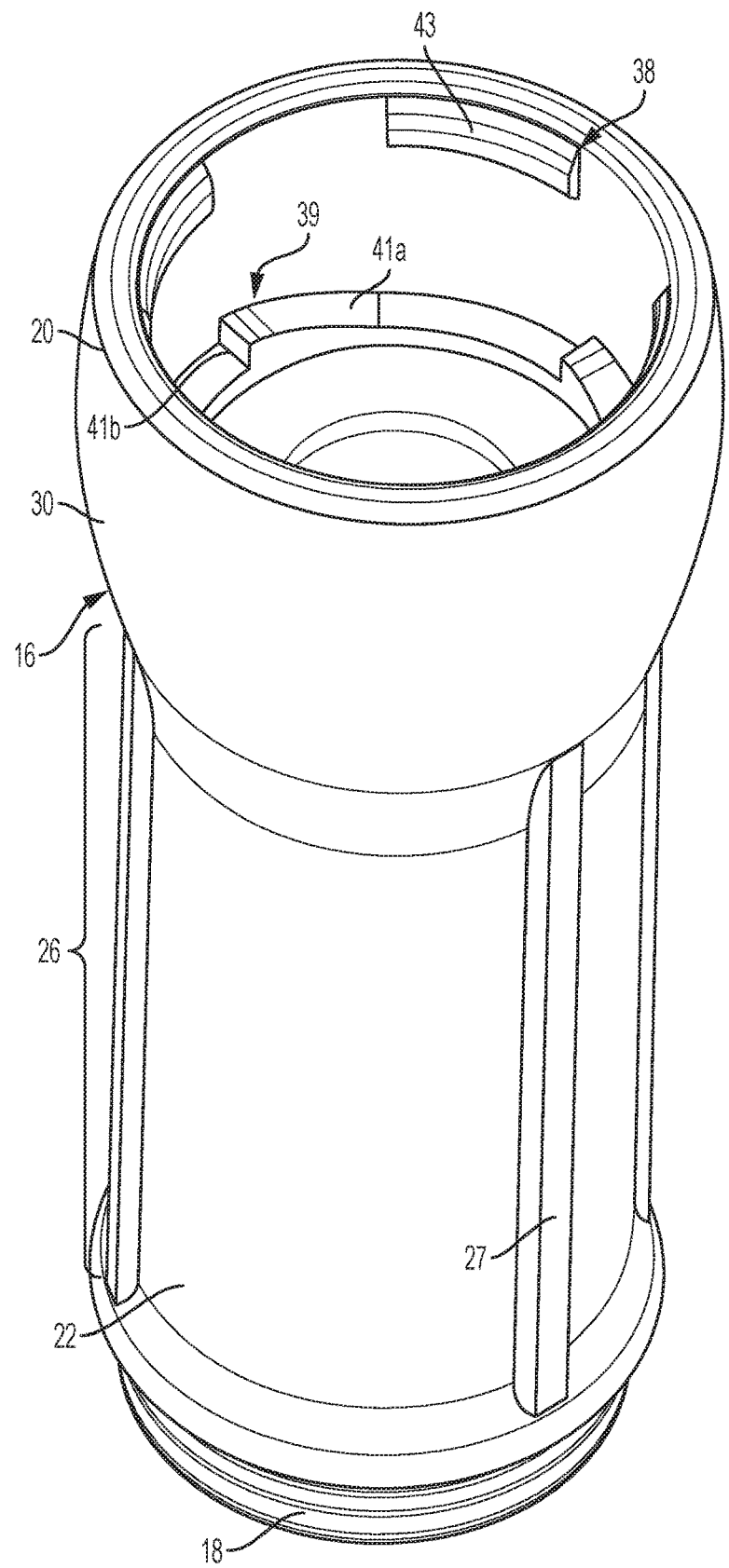
FIG. 7 is a top perspective view of an outer housing of the adapter of FIG. 2 according to an aspect of the invention.
Figure 8:
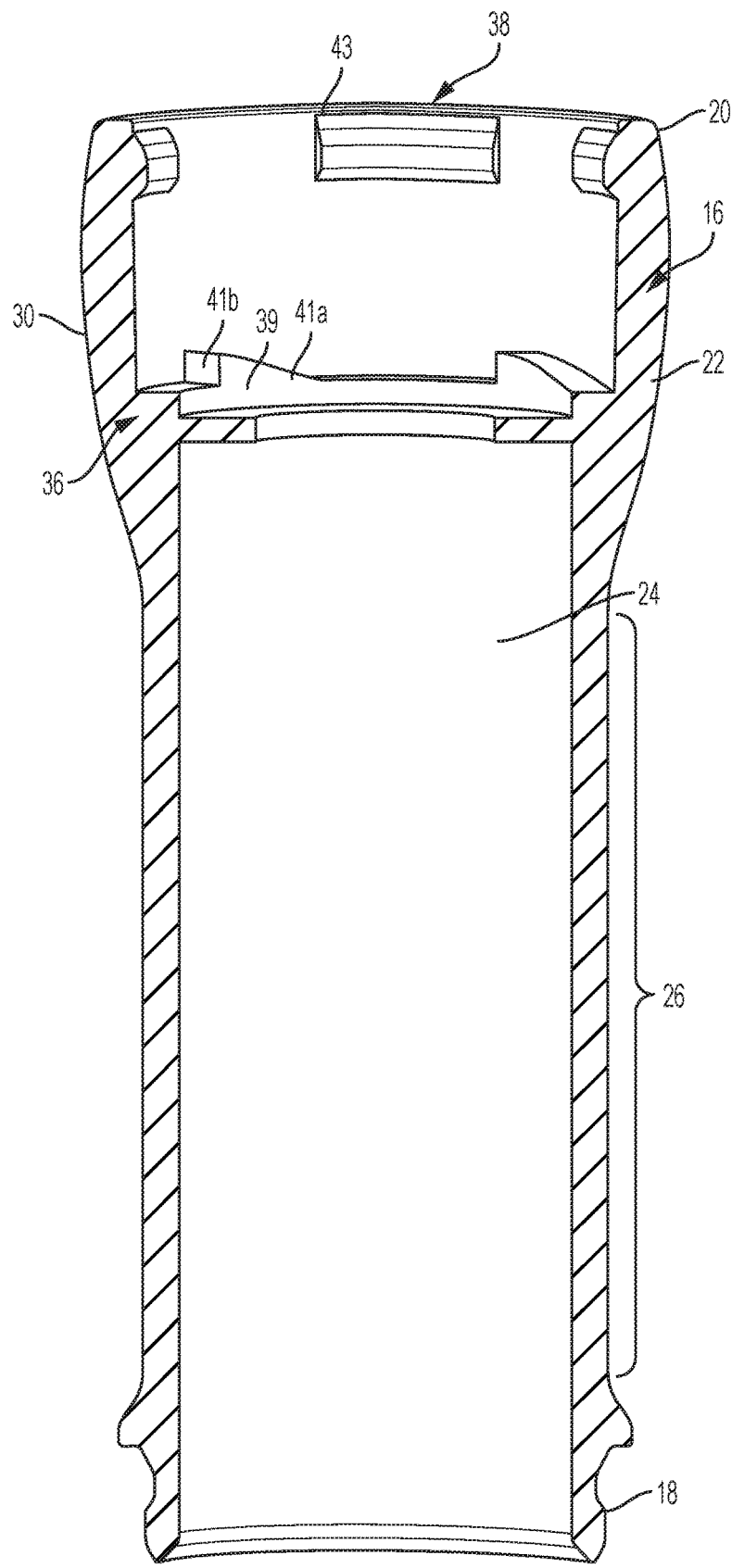
FIG. 8 is a cross-sectional view of the outer housing of FIG. 7.

With reference to FIG. 6, in certain aspects, the housing 16 includes a needle cannula 25 extending therethrough that forms the fluid passageway 24. The cannula 25 may include a tip at a distal end thereof for establishing a fluid connection with a fluid container such as a medical vial. The housing 16 may also include a septum 17 or seal arrangement, capable of being pierced by the tip of the needle, extending across an inner portion of the housing 16. The septum 17 is held within the housing 16 by a holding member 19 that rests on the distal end 18 of the housing 16. A resilient member, such as a spring 21, is also positioned in the housing 16 and rests against a proximal end of the holding member 19 and a flange 23 extending from an inner surface of the housing 16. The spring 21 is biased against the holding member 19 to keep the septum 17 positioned in the housing 16. During use, the needle tip and cannula 25 may be advanced through the septum 17 or seal arrangement to establish fluid communication through the housing 16. The septum 17 or seal arrangement may be configured to prevent fluid from passing through the housing 16 and contaminating other elements of the adapter 10 and/or syringe 4.

The adapter 10 further includes an inner member 28 inserted in the proximal end 20 of the housing 16. For example, in one aspect, the inner member 28 may be inserted in an annular sleeve 30 extending around the proximal end 20 of the housing 16. In one aspect, the inner member 28 rests on a proximal surface of the flange 23. As will be described hereinafter, an inner surface 32 (shown in FIG. 6) of the sidewall 22 may include various structures for engaging the inner member 28 to restrict rotation thereof. The inner member 28 includes a substantially cylindrical body 34 having an outer diameter that generally corresponds with the inner diameter of the sidewall 22 of the housing 16.

With reference to FIG. 6, the body 34 of the inner member 28 is a substantially cylindrical structure, although other suitable shapes may be utilized. The body 34 may include a cap 40 or top on a proximal end thereof. The cap 40 covers a portion of the proximal end of the body 34. The connector 12 extends from the cap 40 of the body 34. A proximal end of the cannula 25 may be inserted into a proximal end of the connector 12 for permitting fluid flow through the housing 16 of the adapter 10. A plurality of teeth 35 extend distally from a distal end 42 of the inner member 28 and are spread around the circumferential surface of the distal end 42 of the inner member 28. Each tooth 35 includes an angled portion 37a and a locking surface 37b that extend substantially perpendicular to and end of the angled portion 37a. It is also contemplated that fewer or additional teeth 35 may be provided on the inner member 28.

The connector 12 includes various structures for connecting the inner member 28 of the adapter 10 to the syringe 4 (shown in FIG. 1). As described above, in one aspect, the exterior sidewall of the connector 12 includes helical threads 14 extending therefrom. The threads 14 are configured to engage corresponding threads 9 on the syringe 4 (shown in FIG. 1). For example, the user may connect the syringe 4 to the connector 10 by twisting the syringe 4 in the first direction A.

The adapter 10 also includes a first locking arrangement 36 that is capable of engaging the housing 16 with the body 34 of the inner member 28 for restricting the inner member 28 from turning in a first direction, such as clockwise, and a second locking arrangement 38 that is capable of engaging the housing 16 with the body 34 of the inner member 28 for restricting the inner member 28 from being retracted in a proximal direction out of the housing 16. In one aspect, the first locking arrangement 36 includes a plurality of teeth 39 extending around an inner circumferential surface of the housing 16. Each tooth 39 includes an angled portion 41a and a locking surface 41b that extends substantially perpendicular to and end of the angled portion 41a.

Figure 2:
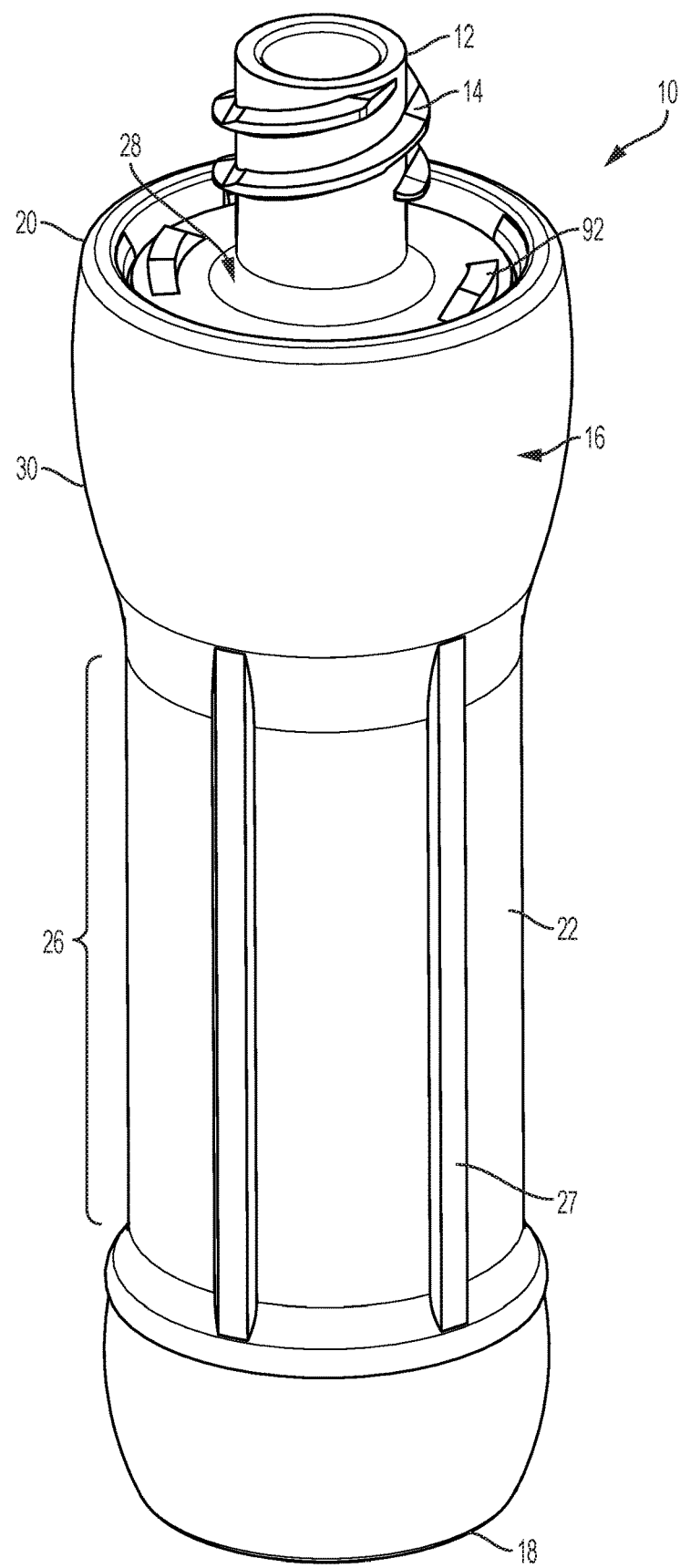
FIG. 2. is a front perspective view of an adapter according to an aspect of the invention.
Figure 3:
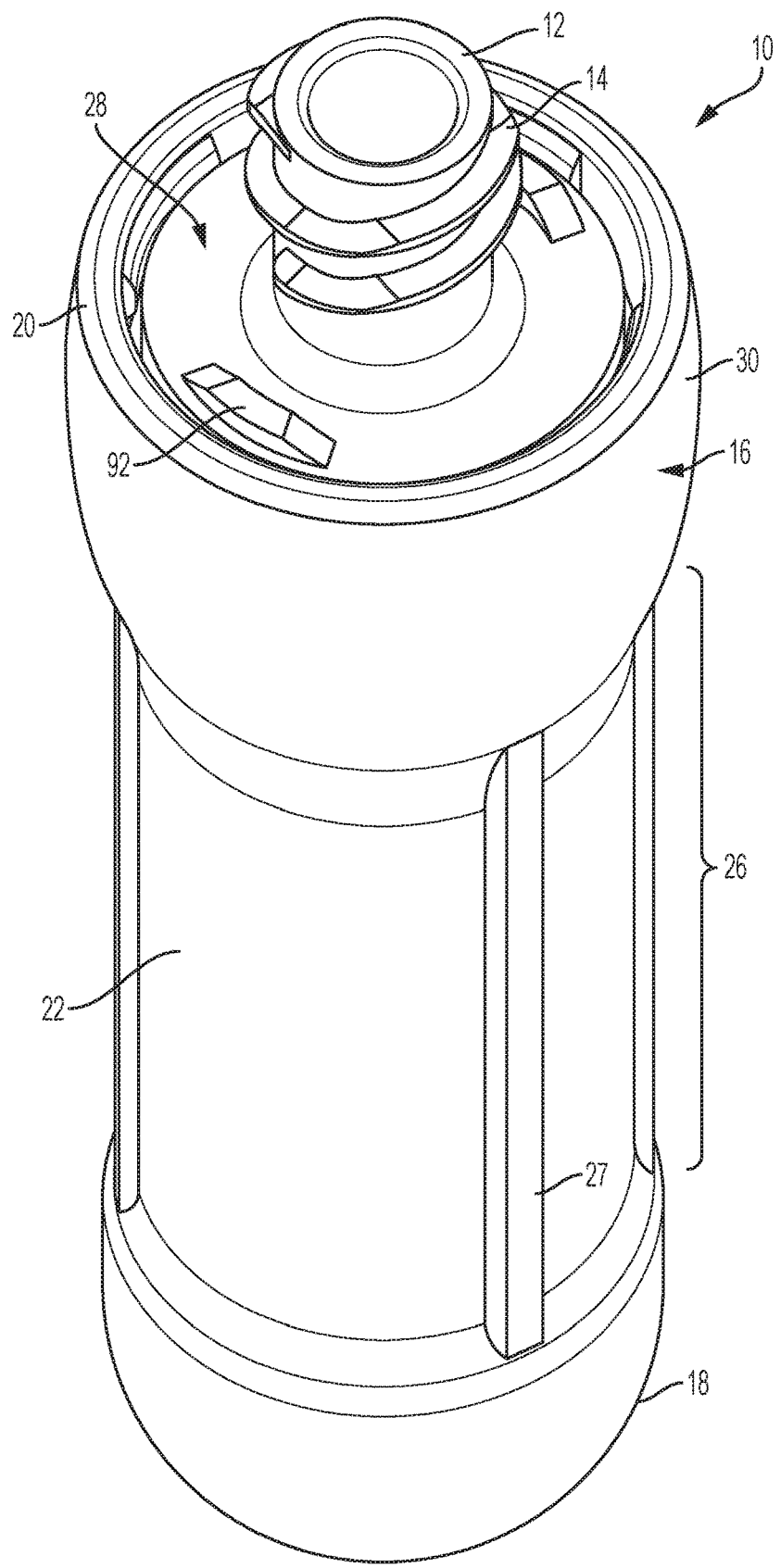
FIG. 3 is a top perspective view of the adapter of FIG. 2.
Figure 4:
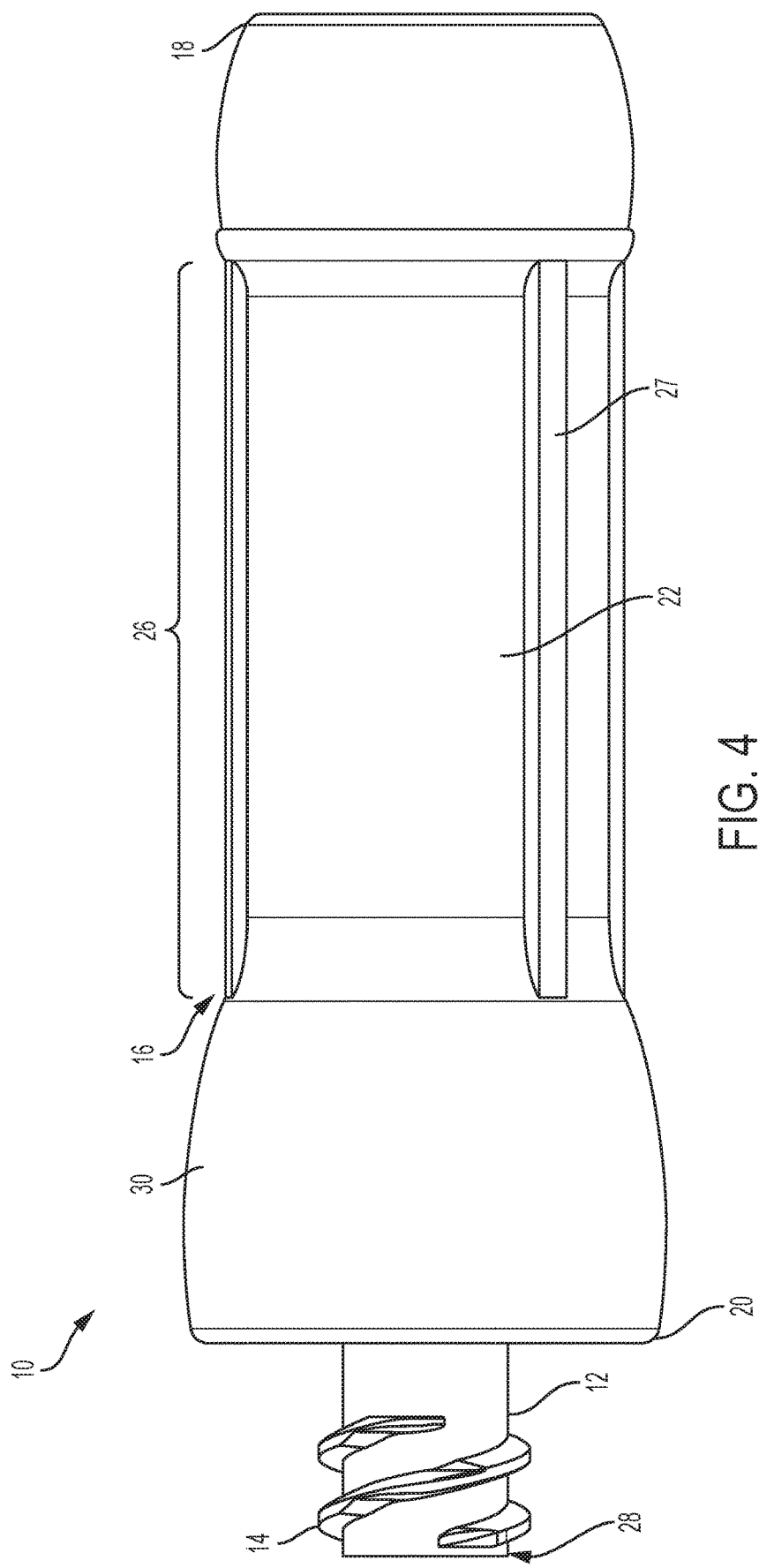
FIG. 4 is a side view of the adapter of FIG. 2.
Figure 5:
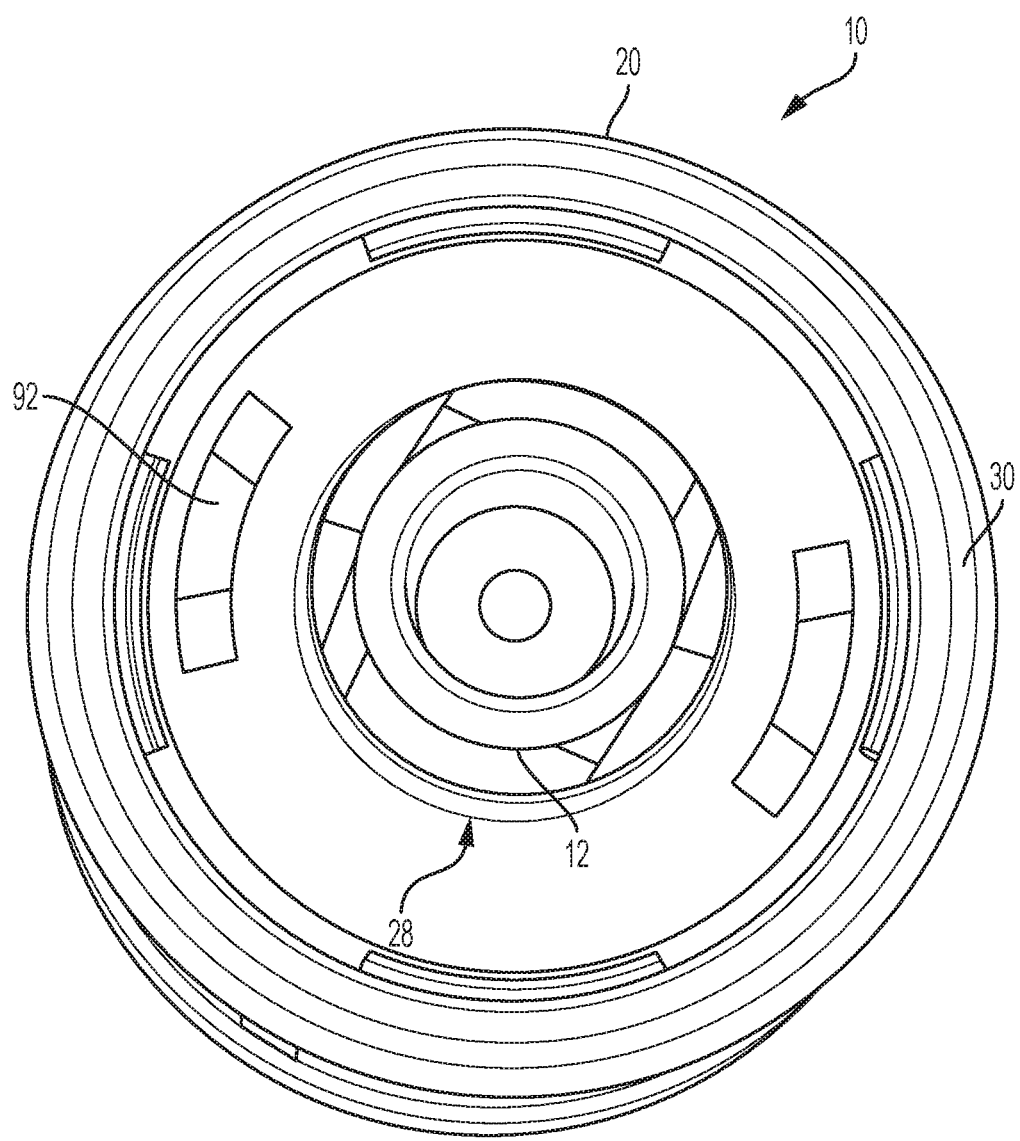
FIG. 5 is a top view of the adapter of FIG. 2.
Figure 9:
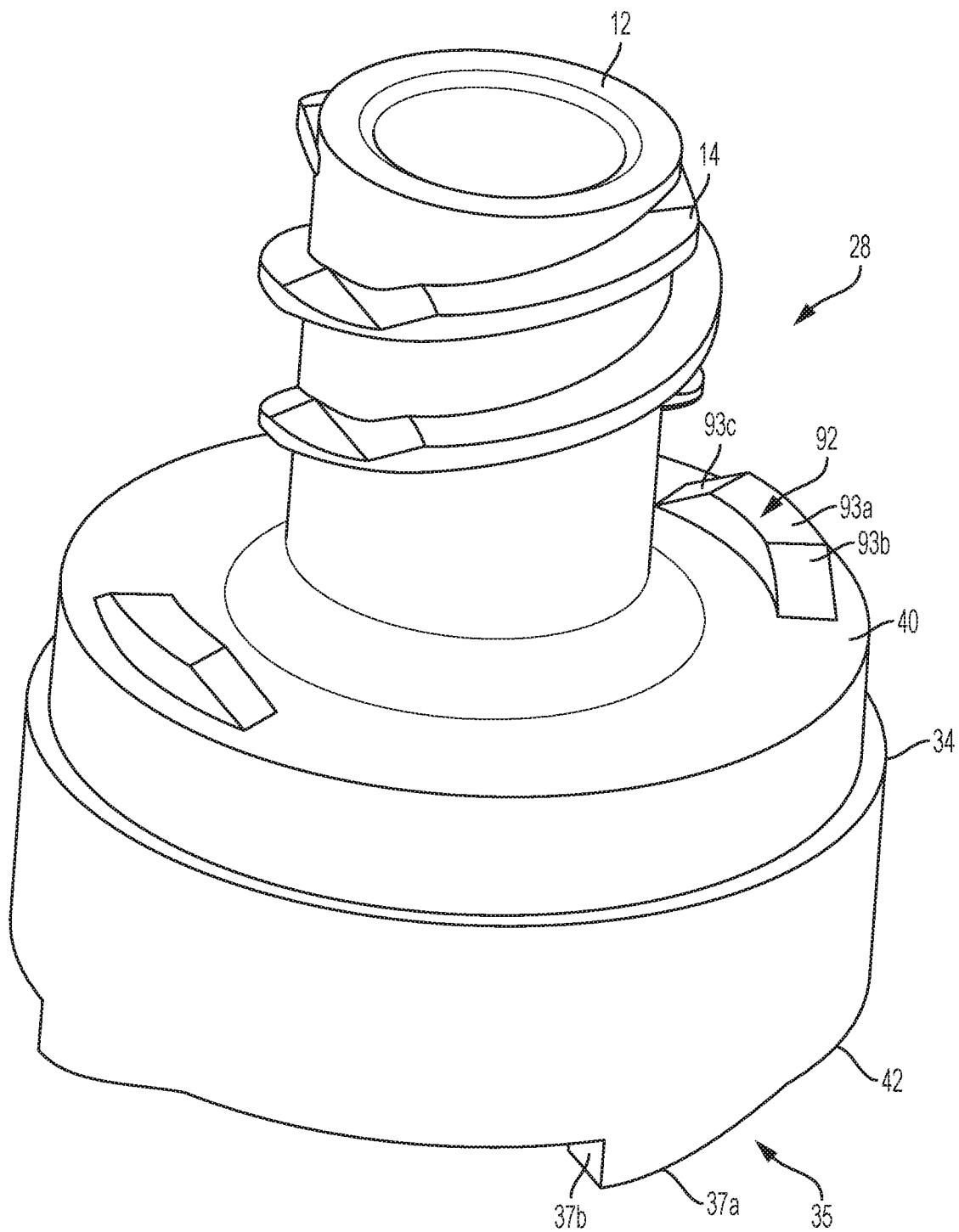
FIG. 9 is a perspective view of an inner member of the adapter of FIG. 2 according to an aspect of the invention.
Figure 22:
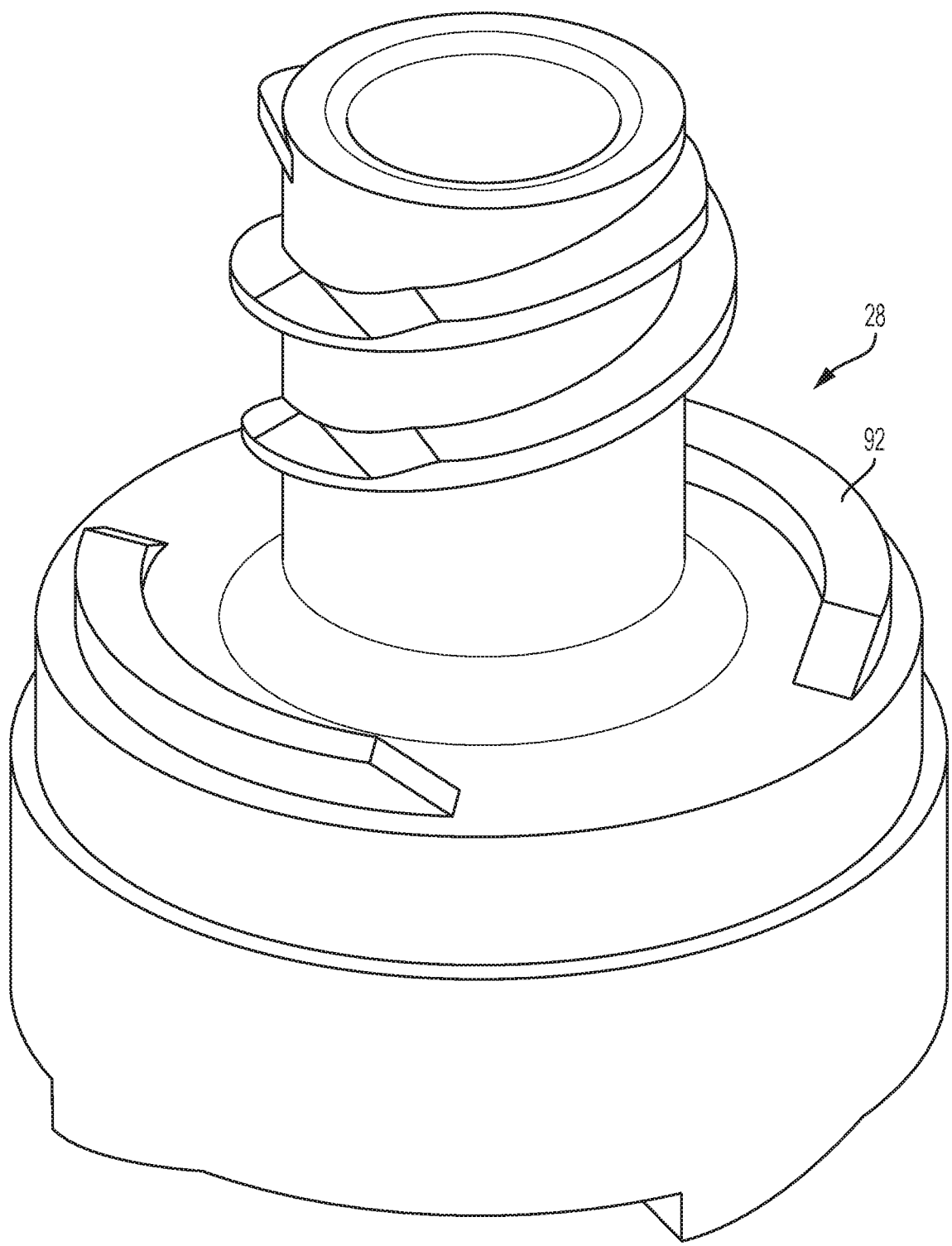
FIG. 22 is a perspective view of an inner member according to another aspect of the invention.

As shown in FIGS. 2, 3, and 9, grasping surfaces, such as one or more flanges 92, may extend from the proximal surface of the cap 40 of the inner member 28. As shown in FIG. 9, in one aspect, two flanges 92 are provided on the cap 40 of the inner member 28. The flanges 92 are positioned 180 degrees from one another on the cap 40. In other aspects, fewer or additional flanges may be provided on the cap 40. The flanges 92 may be positioned at any angular arrangement on the cap 40. In one aspect, the flanges 92 are curved to extend around a portion of the circumferential surface of the cap 40. As shown in FIG. 22, the flanges 92 may extend along a larger portion of the cap 40. When disconnecting the syringe 4 (as described below) from the inner member 28, the user can grasp at least one flange 92 with one hand with sufficient force to prevent the inner member 28 from rotating. The grasping surfaces, such as the flanges 92 illustrated in FIG. 3, may be easier for a user to hold for certain shapes of fluid sources or syringes. Each flange 92 includes a flat, planar portion 93a and two angled portions 93b, 93c. The angled portions 93b, 93c extend from the proximal surface of the cap 40 to the planar portion 93a. The user can grasp or press down on any portion of the flanges 92 to assist the user in preventing rotation of the inner member 28 relative to the housing 16 to disconnect the syringe 4 from the inner member 28.

As will be described in greater detail hereinafter, the adapter 10 is transitionable between three states or positions. First, the adapter 10 may be in a disengaged state, in which the first locking arrangement 36 and the second locking arrangement 38 are not engaged with the inner member 28. In the disengaged state, the inner member 28 can freely rotate relative to the stationary outer housing 16 in both the first direction A and the second direction B. Second, the adapter 10 may be in a first fully engaged state. In the first fully engaged state, the first locking arrangement 36 engages the inner member 28 so that rotation in the first direction A is substantially prevented. Finally, the adapter 10 may be transitioned to a second fully engaged state or position in which the second locking arrangement 38 engages the inner member 28, thereby preventing the inner member 28 from retracting proximally out of the housing 16 while permitting the inner member 28 to rotate freely. It is noted, however, that some rotation may still occur in the partially engaged and fully engaged states if the locking arrangements 36, 38 have not reached a hard stop or if the user is not gripping the locking arrangements 36, 38 strongly enough to fully prevent rotation of the inner member 28.

Figure 10:
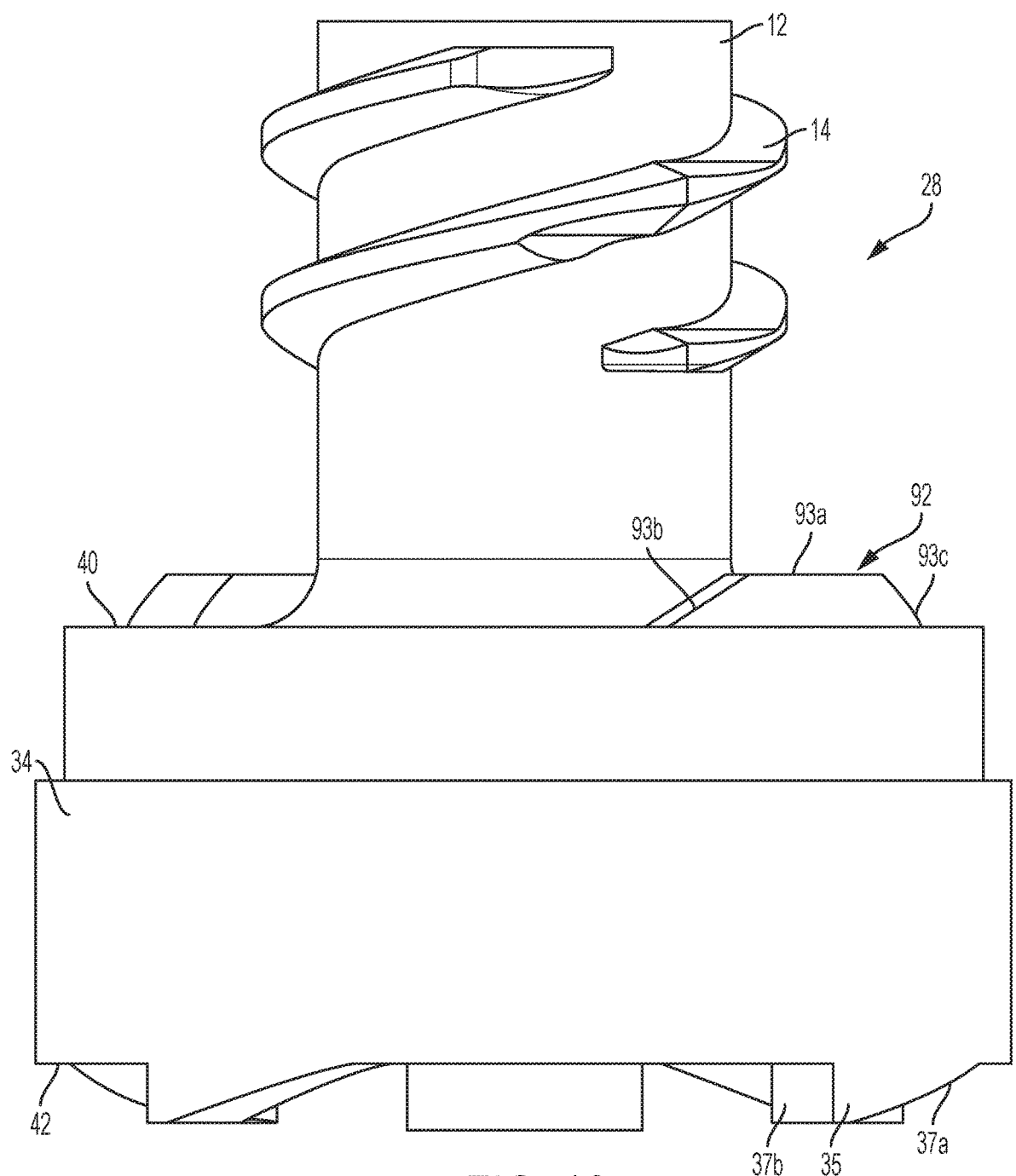
FIG. 10 is a side view of the inner member of FIG. 9.
Figure 11:
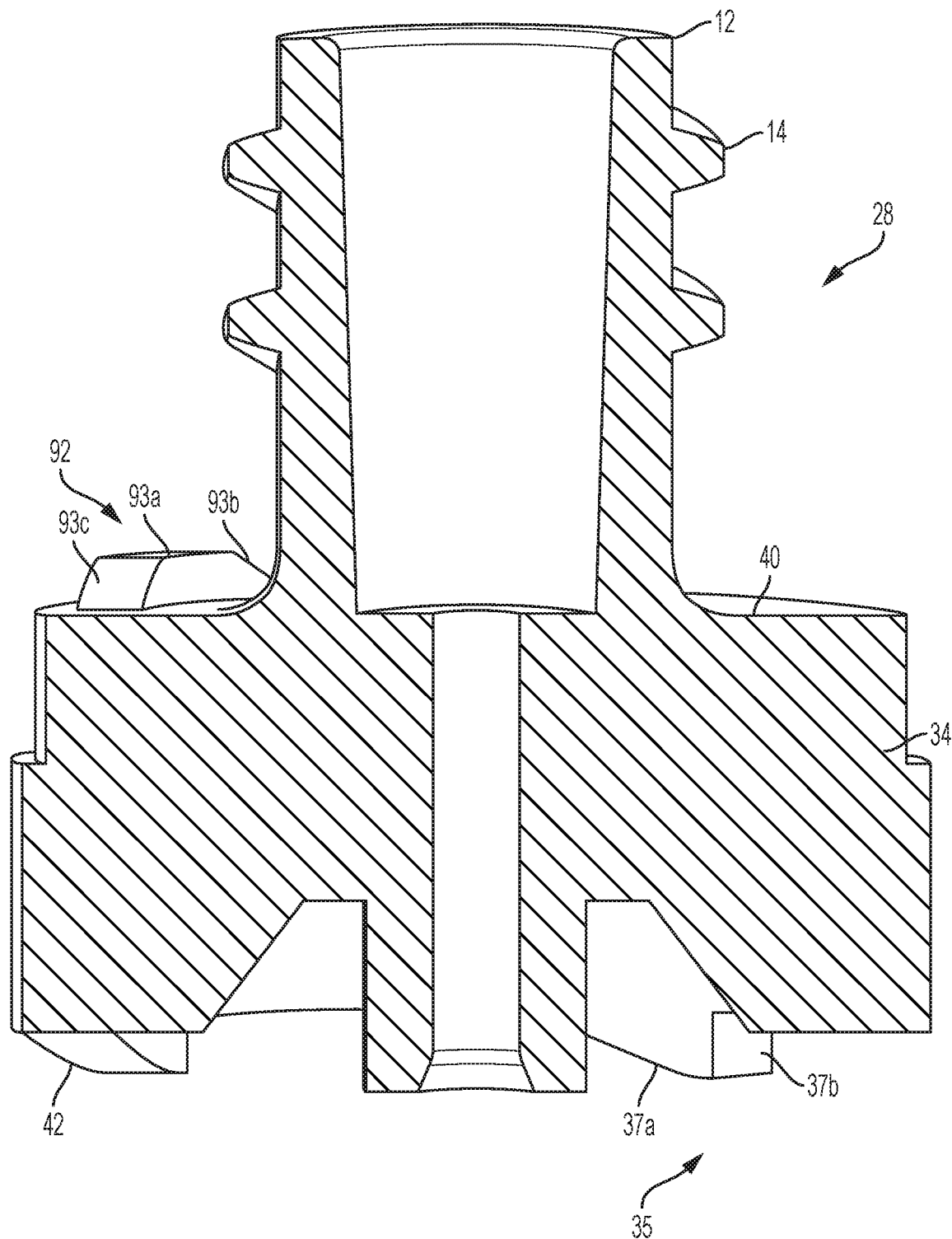
FIG. 11 is a cross-sectional view of the inner member of FIG. 9.

With reference to FIGS. 6 and 10, the inner member 28 is configured to be transitionable from an extended position to a recessed position in which the inner member 28 is inserted farther into the outer housing 16. The user advances the inner member 28 in the distal direction D, relative to the housing 16, to transition the inner member 28 from the extended position to the recessed position by applying a compressive force thereto. As will be described hereinafter, the first locking arrangement 36 cannot engage the inner member 28 when it is in the extended position. When the inner member 28 is in the recessed position, the first locking arrangement 36 is capable of engaging the inner member 28 to restrict rotation of the inner member 28 relative to the outer housing 16 in the first direction A. The inner member 28 is inserted into the housing 16 until the inner member 28 rests on the first locking arrangement 36. After the inner member 28 has been positioned against the flange 23, the inner member 28 is rotated or ratcheted until the teeth 35 extending from a distal end 42 of the inner member 28 engage the teeth 39 extending from the housing 16. Upon interconnection between the teeth 35, 39, the inner member 28 is permitted to rotate in the second direction B, but not the first direction A. The locking surfaces 37b of the teeth 35 abut the locking surfaces 41b of the first locking arrangement 36 to prevent rotation in the first direction A. During insertion and rotation of the inner member 28 within the housing 16, the teeth 35 of the inner member 28 are directed upwards along the angled portions 41a of the teeth 39 of the housing 16 so that the inner member 28 is permitted to freely rotate in the second direction B. However, when the inner member 28 is rotated in the first direction A, the locking surfaces 37b of the teeth 35 of the inner member 28 abut the locking surfaces 41b of the teeth 39 of the housing 16, such that rotation of the inner member 28 in the first direction A is prevented. Therefore, as a practitioner rotates the syringe 4 onto the inner member 28, the inner member 28 is prevented from rotating in the first or clockwise direction A to hold the inner member 28 stationary relative to the syringe 4 so the syringe 4 can be twisted onto the inner member 28. However, since the inner member 28 is not prevent from rotating in the second direction B, the inner member 28 cannot be held stationary relative to the syringe 4 to permit the practitioner to rotate the syringe 4 in a counterclockwise direction to disconnect the syringe 4 from the inner member 28. Using this arrangement, an unintentional or accidental disconnection of the syringe 4 from the inner member 28 is prevented.

Further, as the inner member 28 is inserted into the housing 16, the second locking arrangement 38 engages the cap 40 of the inner member 28 to prevent proximal movement of the inner member 28 in the housing 16. In one aspect, the second locking arrangement 38 includes a plurality of locking tabs 43 that extend around an inner circumferential surface of the housing 16. As the inner member 28 is advanced into the housing 16, the cap 40 is pushed past the locking tabs 43 to push the locking tabs 43 outwardly. Once the cap 40 advances past the locking tabs 43, the locking tabs 43 move inwardly to engage the upper surface of the cap 40, thereby preventing proximal movement of the inner member 28 out of the housing 16.

As described above, the adapter 10 of the present disclosure is configured to require a compound motion or activity to disconnect the syringe 4 (shown in FIG. 1) from the adapter 10. In a preferred and non-limiting aspect of the adapter 10, the first activation motion or maneuver is considered to be pressing the inner member 28 in the distal direction D with a compressive force that is sufficient to push the inner member 28 past the locking tabs 43.

With reference to FIG. 6, to connect the syringe 4 to the adapter 10, the user grasps the syringe 4 in a conventional manner. The user aligns the distal portion of the syringe 4 with the connector 12 of the adapter 10, such that helical threads 14 of the connector 12 contact corresponding threads 9 on the shield surrounding the male luer lock 6 of the syringe 4. It is noted, however, that since the adapter 10 is in the disengaged position, the inner member 28 spins freely in the second direction B. Therefore, if the user were to try to turn the syringe 4 in a counterclockwise direction relative to the connector 12, the inner member 28 would also rotate preventing connection therebetween. Instead, the user must press the syringe 4 against the connector 12 in distal direction D with sufficient compressive force to insert the inner member 28 into the housing 16. Once sufficient force is applied, the inner member 28 is transitioned to the recessed position.

In the recessed position, the teeth 35 (shown in FIGS. 9 and 10) of the first locking arrangement 36 and the teeth 39 of the housing 16 are brought into contact with one another. More specifically, once the inner member 28 is in the recessed position, the user can slightly rotate the inner member 28 relative to the housing 16 to established contact and/or engagement between the teeth 35 of the inner member 28 and the teeth 39 extending from the housing 16. Once the engagement between the inner member 28 and the housing 16 is established, the inner member 28 is prevented from rotating any farther in the first direction A. Thus, the user can rotate the syringe 4 in direction A relative to the connector 12 to engage the threads 9 of the syringe 4 with the corresponding helical threads 14 of the connector 12. Since the inner member 28 is fixedly engaged with the first locking arrangement 36, twisting the syringe 4 in direction A does not cause the inner member 28 to rotate.

Once the syringe 4 is sufficiently tightly connected to the connector 12 of the inner member 28, the user can release the syringe 4. In this position, the inner member 28 and syringe 4 attached thereto can freely rotate in the first direction A and/or second direction B relative to the housing 16. Furthermore, since the inner member 28 and/or syringe 4 rotate freely in the second direction B, it would be rather difficult or impossible for the user to remove the syringe 4 from the connector 12 of the inner member 28 when it is in the extended position. Thus, the chance that the user or patient could inadvertently remove the syringe 4 from the adapter 10 is effectively reduced.

To remove the syringe 4 from the adapter 10, the user first pushes the syringe 4 toward the adapter 10, in the same manner described above, to transition the inner member 28 from the extended position to the recessed position. This action is referred to as the first motion or maneuver. Specifically, to disconnect the syringe 4 from the connector 12, the user must rotate the syringe 4 in the second direction B. However, when the adapter 10 is in the first fully engaged position in which it cannot rotate in the first direction A, the inner member 28 is free to rotate in the second direction B, meaning that removing the syringe 4 from the connector 12 would be difficult or prevented. Therefore, the user must press the cap 40 of the inner member 28 downwardly to press the inner member 28 against the flange 23. Pressing the cap 40 is referred to as the second motion or maneuver. By pressing the inner member 28 against the first locking arrangement 36, the inner member 28 and, thereby, the syringe 4 are prevented from rotating in either direction due to friction established between the inner member 28 and the first locking arrangement 36. Since, in this position, the inner member 28 is prevented from rotating in the second direction B, the user can easily twist the syringe 4 in the second direction B to unscrew it from the connector 12. Unscrewing the syringe 4 from the connector 12 is referred to as the third motion of maneuver.

Figure 12:
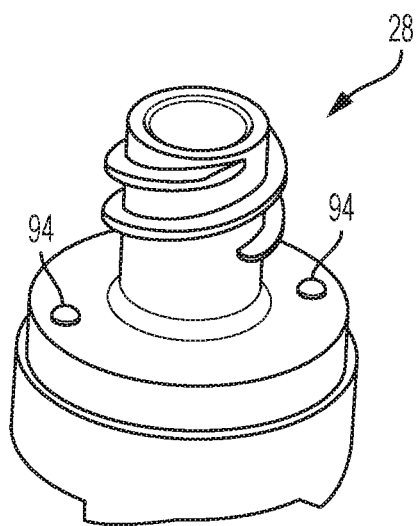
FIG. 12 is a perspective view of an inner member according to another aspect of the invention.
Figure 13:
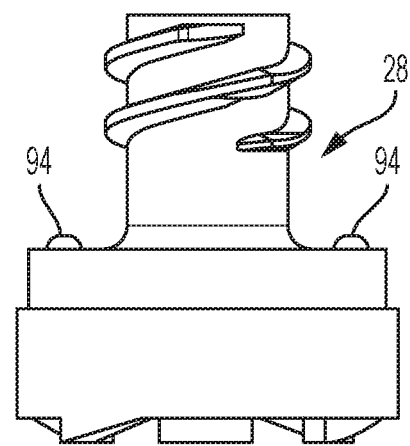
FIG. 13 is a side view of the inner member of FIG. 12.
Figure 14:
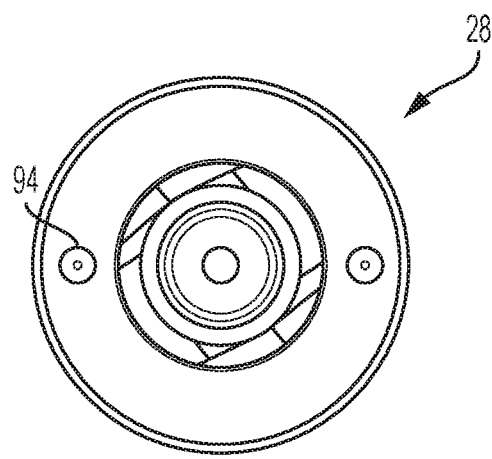
FIG. 14 is a top view of the inner member of FIG. 12.

With reference to FIGS. 12-24, additional arrangements for preventing rotation of the inner member 28 relative to the housing 16 to disconnect the syringe 4 from the inner member 28 are shown and described. As shown in FIGS. 12-14, the inner member 28 includes the same features as the inner member 28 described above in FIGS. 1-11. The flanges 92 of the inner member 28, however, are replaced with bumps 94 that extend from the proximal surface of the cap 40. The bumps 94 have a hemispherical shape that is raised from the proximal surface of the cap 40. The bumps 94 have substantially rounded edges to provide a smooth surface for a user to press down on when disconnecting the syringe 4 from the inner member 28. In one aspect, two bumps 94 are provided on the cap 40. The bumps 94 are spaced 180 degrees apart from one another on the cap 40. It is also contemplated, however, that fewer or additional bumps may be provided on the cap 40 at any different angular arrangement.

Figure 15:
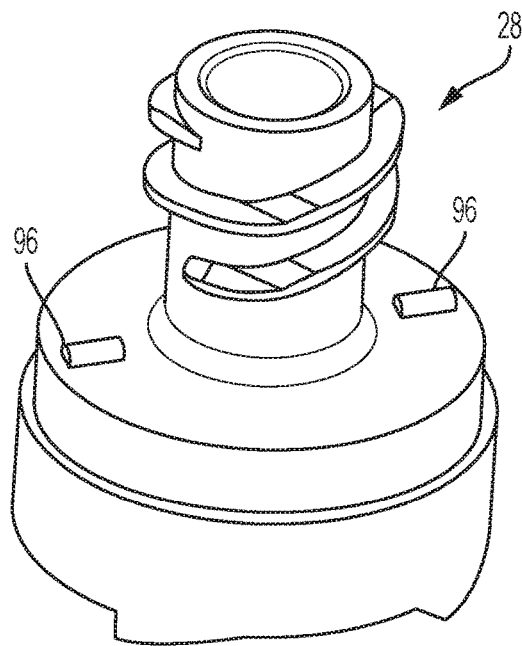
FIG. 15 is a perspective view of an inner member according to another aspect of the invention.
Figure 16:
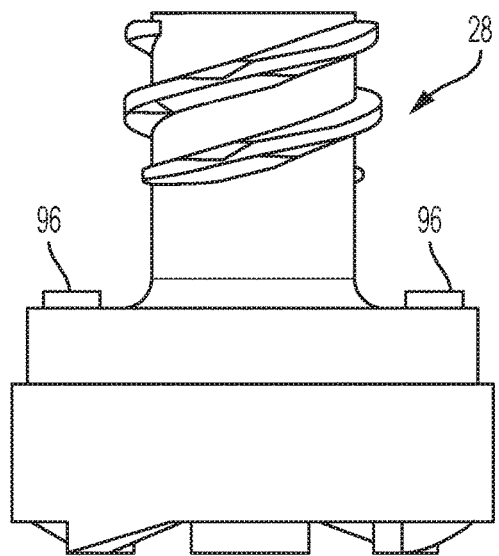
FIG. 16 is a side view of the inner member of FIG. 15.
Figure 17:
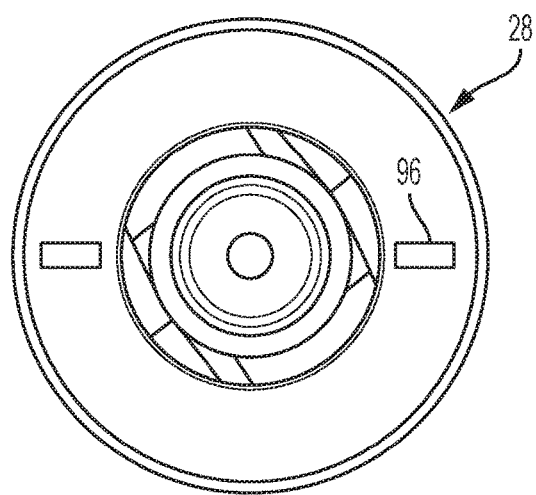
FIG. 17 is a top view of the inner member of FIG. 15.

As shown in FIGS. 15-17, the inner member 28 includes the same features as the inner member 28 described above in FIGS. 1-11. The flanges 92 of the inner member 28, however, are replaced with tabs 96 that extend from the proximal surface of the cap 40. The tabs 96 include a planar portion that extends parallel to the proximal surface of the cap 40 and two curved portions that extend from the proximal surface of the cap 40 to connect to the planar portion. The curved portions have substantially rounded edges to provide a smooth surface for a user to press down on when disconnecting the syringe 4 from the inner member 28. In one aspect, two tabs 96 are provided on the cap 40. The tabs 96 are spaced 180 degrees apart from one another on the cap 40 and extend horizontally relative to the connector 12 of the inner member 28. It is also contemplated, however, that fewer or additional tabs may be provided on the cap 40 at any different angular arrangement.

Figure 18:
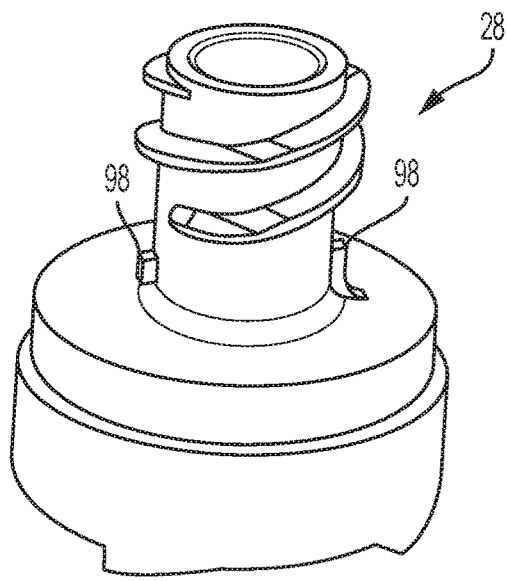
FIG. 18 is a perspective view of an inner member according to another aspect of the invention.
Figure 19:
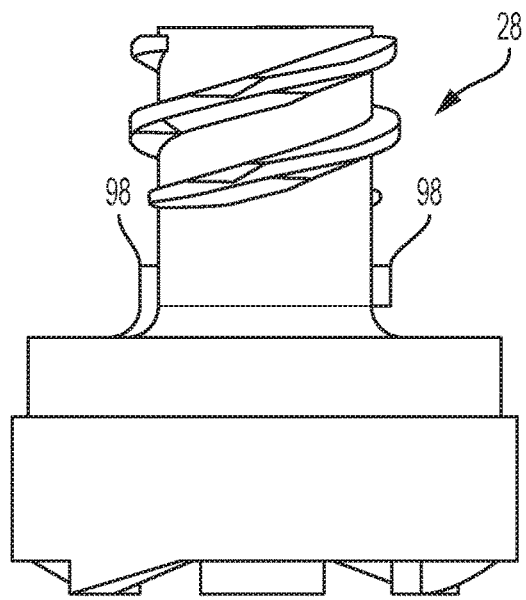
FIG. 19 is a side view of the inner member of FIG. 18.
Figure 20:
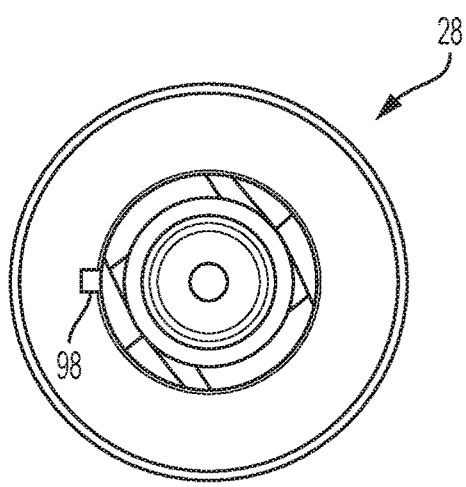
FIG. 20 is a top view of the inner member of FIG. 18.
Figure 21:
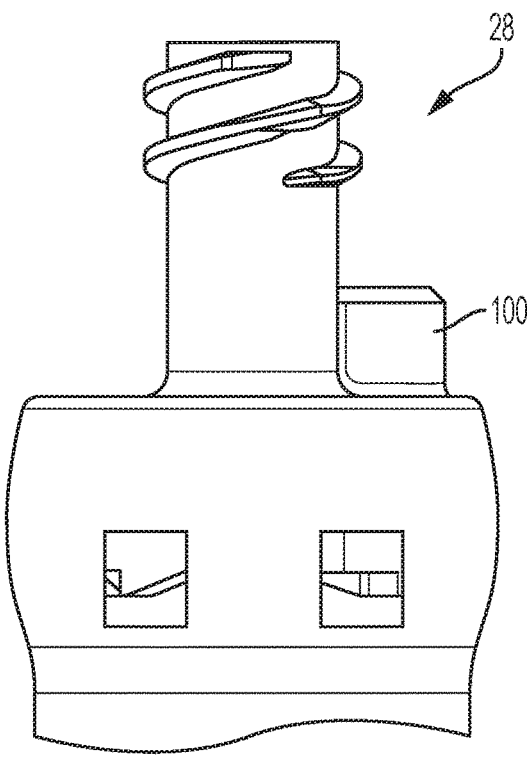
FIG. 21 is a side view of an alternative aspect of the inner member of FIG. 18.

As shown in FIGS. 18-20, the inner member 28 includes the same features as the inner member 28 described above in FIGS. 1-11. The flanges 92 of the inner member 28, however, are replaced with vertical flanges 98 that extend from the connector 12 of the inner member 28. The vertical flanges 98 extend vertically along a portion of a side surface of the connector 12. One of the vertical flanges 98 is substantially rectangular and includes a plurality of grasping surfaces that permit a user to stop rotation of the inner member 28 relative to the housing 16. Another of the vertical flanges 98 includes a portion that extends vertically along a portion of the side surface of the connector 12 and a portion that extends horizontally along the proximal surface of the cap 40. In this arrangement, the vertical flange 98 is positioned on the cap 40 and the connector 12. In one aspect, two vertical flanges 98 are provided on the connector 12. The vertical flanges 98 are spaced 180 degrees apart from one another on the connector 12 and extend vertically relative to the connector 12 of the inner member 28. It is also contemplated, however, that fewer or additional vertical flanges may be provided on the connector 12 at any different angular arrangement. Further, as shown in FIG. 21, a thumb stop 100 may be provided on one of the vertical flanges 98. The thumb stop 100 may extend vertically from the cap 40 and horizontally from the connector 12 to provide a larger surface for the user to grasp to prevent rotation of the inner member 28 relative to the housing 16. The user can press or hold the thumb stop 100 to prevent the inner member 28 from rotating in the second direction B to allow disconnection of the syringe 4 from the inner member 28.

Figure 24:
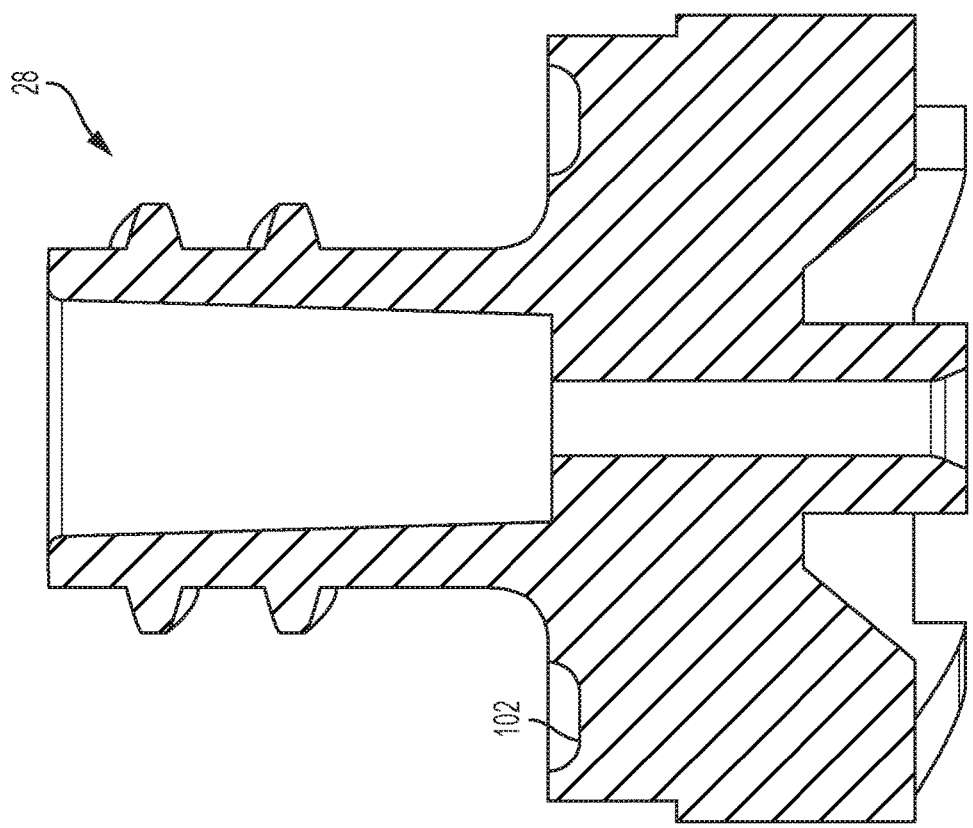
FIG. 24 is a cross-sectional view of the inner member of FIG. 23.
Figure 23:
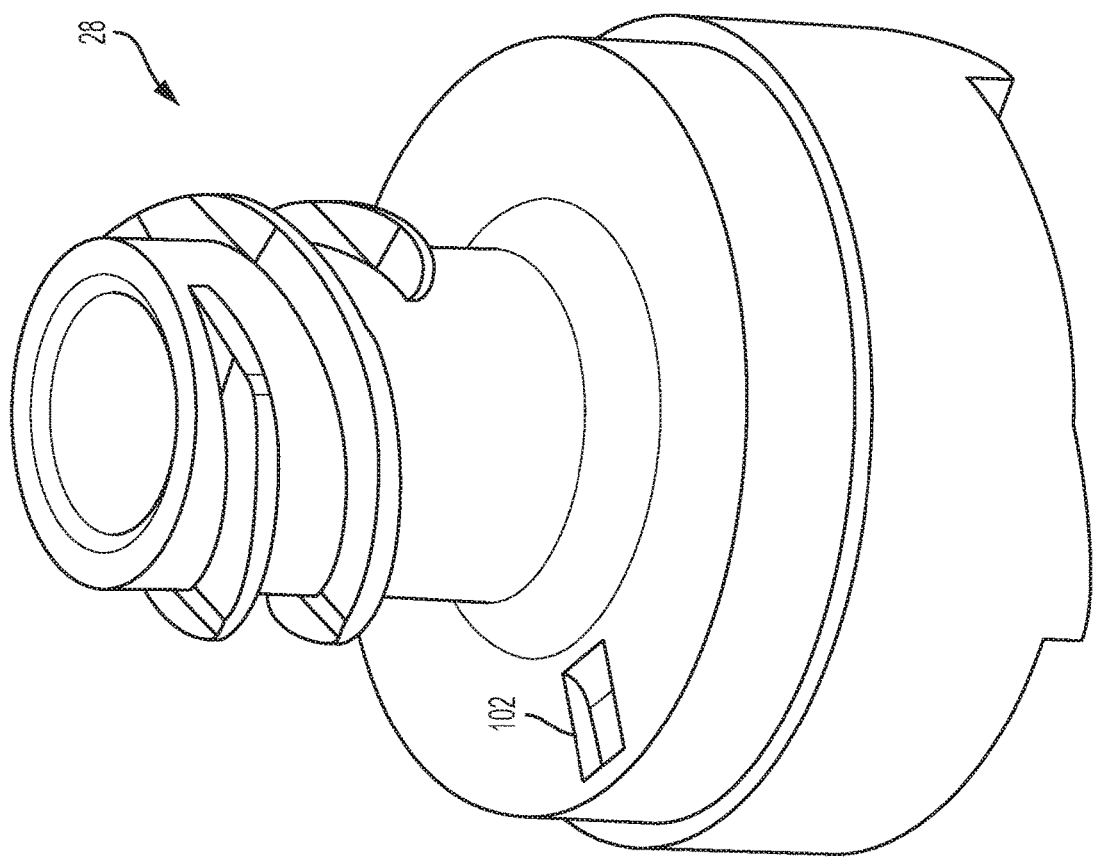
FIG. 23 is a perspective view of an inner member according to another aspect of the invention.
Figure 25:
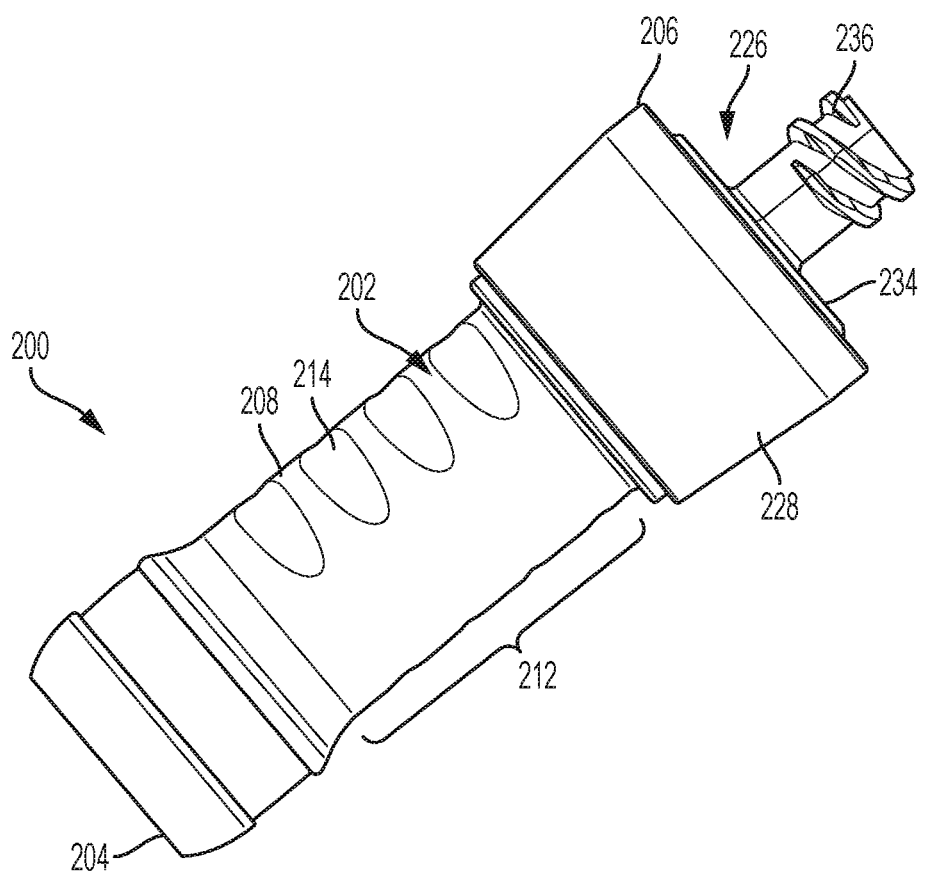
FIG. 25 is a perspective view of an adapter according to another aspect of the disclosure.
Figure 26:
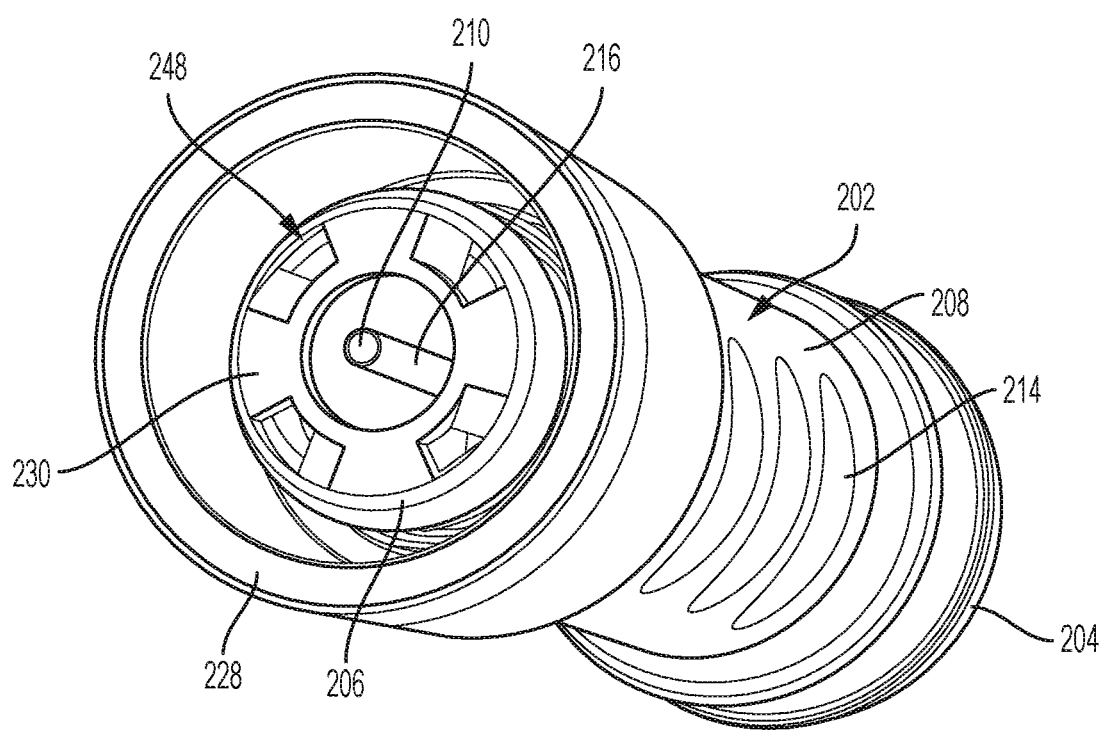
FIG. 26 is a perspective view of the adapter of FIG. 25 with an inner member removed.

As shown in FIGS. 23 and 24, the inner member 28 includes the same features as the inner member 28 described above in FIGS. 1-11. The flanges 92 of the inner member 28, however, are replaced with a groove 102 defined in the proximal surface of the cap 40. The groove 102 includes a flat bottom surface, two curved side surfaces, and two vertical side surfaces. The groove 102 is configured to permit a user to insert a finger or tool into the groove 102 to prevent rotation of the inner member 28 relative to the housing 16 to disconnect the syringe 4 from the inner member 28. By defining a groove 102 in the cap 40, no external grasping surface extends from the proximal surface of the cap 40. In one aspect, one groove 102 is defined in the cap 40. It is also contemplated, however, that additional grooves may be defined in the cap 40 at any different angular arrangement.

With reference to FIGS. 25-29, another aspect of the adapter 200 according to the present disclosure is described. The adapter 200 is similar in construction and function as the adapter 10 described above, but with a few differences as described below. The adapter 200 includes an outer housing 202 having a distal end 204, a proximal end 206, and a generally cylindrical sidewall 208 extending between the distal end 204 and the proximal end 206. A needle extending through the housing 202 defines a fluid passageway 210 (shown in FIG. 26) extending between the proximal end 206 and distal end 204 of the outer housing 202. The housing 202 may be formed from any suitable structural material including medical grade plastic or metal. Optionally, the housing 202 may include various features that make holding or manipulating the housing 202 and adapter 200 easier. For example, the housing 202 may include a narrower grip portion 212 that is more comfortable for users to hold. The housing 202 may also include a plurality of indentations 214 that are sized and shaped to receive a user's fingers during use of the adapter 200 so that the housing 202 does not slip or slide when held by the user. The housing 202 may also include various aesthetic features such as patterns, designs, logos, and the like for improving the appearance of the outer housing 202.

Figure 27:
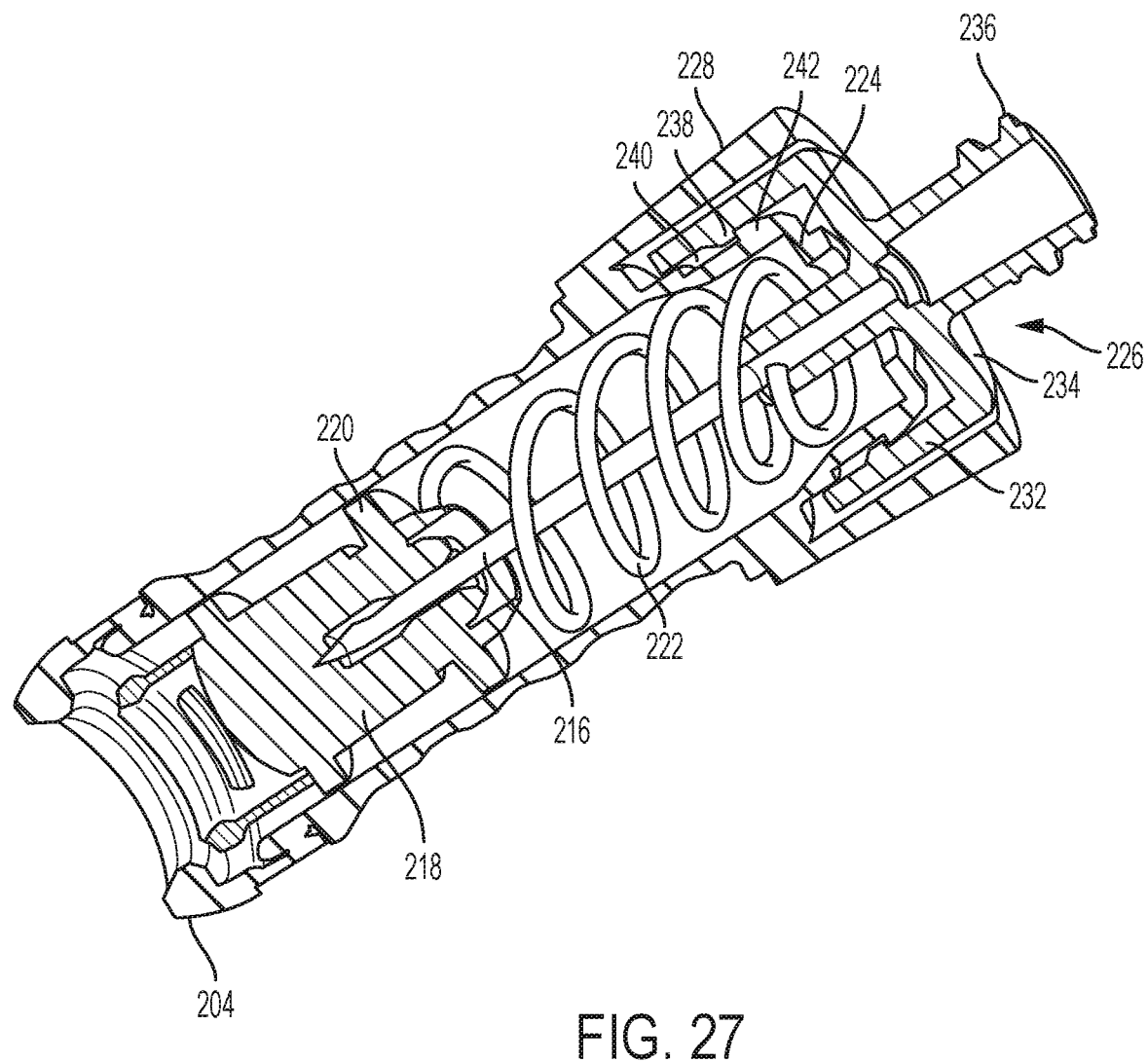
FIG. 27 is a cross-sectional view of the adapter of FIG. 25.

With reference to FIG. 27, in certain aspects, the housing 202 includes a needle cannula 216 extending therethrough that forms the fluid passageway 210. The cannula 216 may include a tip at a distal end thereof for establishing a fluid connection with a fluid container such as a medical vial. The housing 202 may also include a septum 218 or seal arrangement, capable of being pierced by the tip of the needle, extending across an inner portion of the housing 202. The septum 218 is held within the housing 202 by a holding member 220 that rests on the distal end 204 of the housing 202. A resilient member, such as a spring 222, is also positioned in the housing 202 and rests against a proximal end of the holding member 220 and a flange 224 extending from an inner surface of the housing 202. The spring 222 is biased against the holding member 220 to keep the septum 218 positioned in the housing 202. During use, the needle tip and cannula 216 may be advanced through the septum 218 or seal arrangement to establish fluid communication through the housing 202. The septum 218 or seal arrangement may be configured to prevent fluid from passing through the housing 202 and contaminating other elements of the adapter 200.

The adapter 200 further includes an inner member 226 inserted in the proximal end 206 of the housing 202. For example, in one aspect, the inner member 226 may be inserted in a hub cover 228 extending around the proximal end 206 of the housing 202. In one aspect, the inner member 226 rests on a proximal surface of the flange 224. As will be described hereinafter, an inner surface 230 (shown in FIG. 28) of the sidewall 208 may include various structures for engaging the inner member 226 to restrict rotation thereof. The inner member 226 includes a substantially cylindrical body 232 having an outer diameter that generally corresponds with the inner diameter of the hub cover 228 of the housing 202. The hub cover 228 is made of a substantially flexible material so that the hub cover 228 is configured to be pressed inwardly upon pressure applied by a user. After the pressure has been released by the user, the hub cover 228 will expand back to its original resting position. In one aspect, the hub cover 228 is made of a flexible, resilient plastic material.

Figure 29:
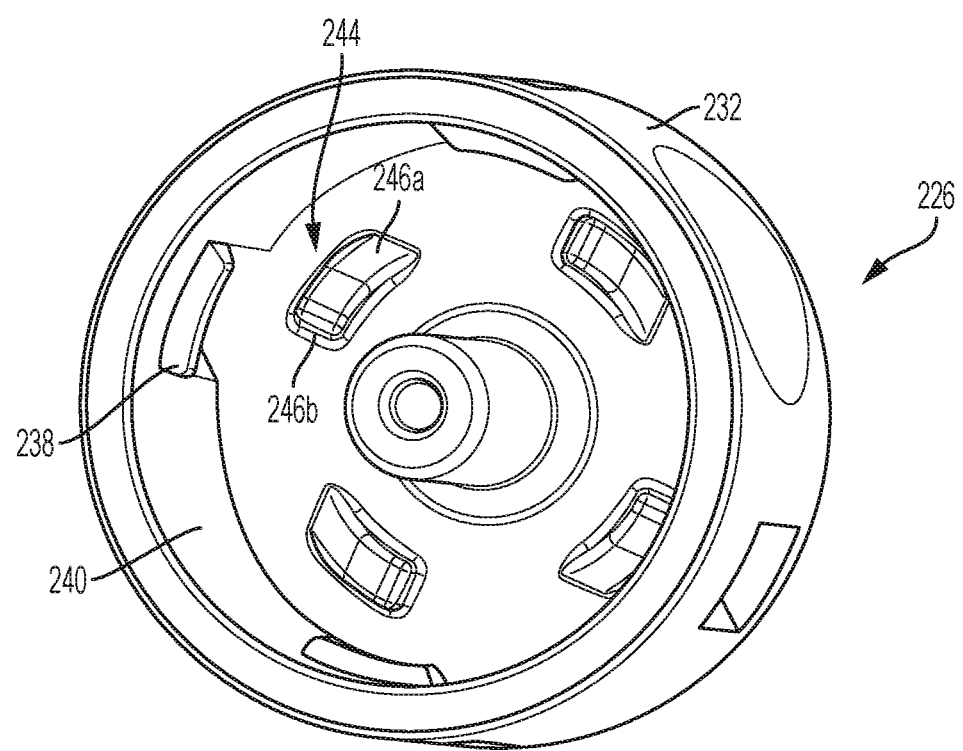
FIG. 29 is a bottom perspective view of the inner member of the adapter of FIG. 25.

With reference to FIGS. 27 and 29, the body 232 of the inner member 226 is a substantially cylindrical structure, although other suitable shapes may be utilized. The body 232 may include a cap 234 or top on a proximal end thereof. The cap 234 covers a portion of the proximal end of the body 232. A connector 236 extends from the cap 234 of the body 232 and is positioned such that the fluid passageway 210 extends therethrough. For example, a proximal end of the cannula 216 may be inserted into a proximal end of the connector 236 for permitting fluid flow through the needle of the adapter 200. A plurality of locking tabs 238 (also referred to as a second locking arrangement) extend inwardly from an inner surface 240 of the inner member 236 and are spread around the circumferential surface of the inner surface 240 of the inner member 236. As shown in FIG. 27, when the adapter 200 is assembled, the inner member 226 is inserted into the hub cover 228. As the inner member 226 is inserted into the hub cover 228, the locking tabs 238 are pushed outwardly by sliding along a locking protrusion 242 that extends around an outer surface of the sidewall 208. After the locking tabs 238 are pushed past the locking protrusion 242, the locking tabs 238 snap back into place and are held a distal surface of the locking protrusion 242. When in the locked position, the inner member 236 is prevented from being displaced proximally within the hub cover 228, but is permitted to rotate within the hub cover 228. Further, the inner surface 230 also prevents the spring 222 from biasing the inner member 226 upwards.

With reference to FIG. 29, a first locking arrangement of the adapter 200 includes a plurality of teeth 244 extending from the proximal end of an inner surface of the inner member 226. In one aspect, a total of four teeth 244 are provided on the inner surface of the inner member 226. The teeth 244 are spread in a circular pattern around the inner surface of the inner member 226. Each tooth 244 includes an angled portion 246a and a locking surface 246b that extend substantially perpendicular to an end of the angled portion 246a. It is also contemplated that fewer or additional teeth 244 may be provided on the inner member 226.

Figure 28:
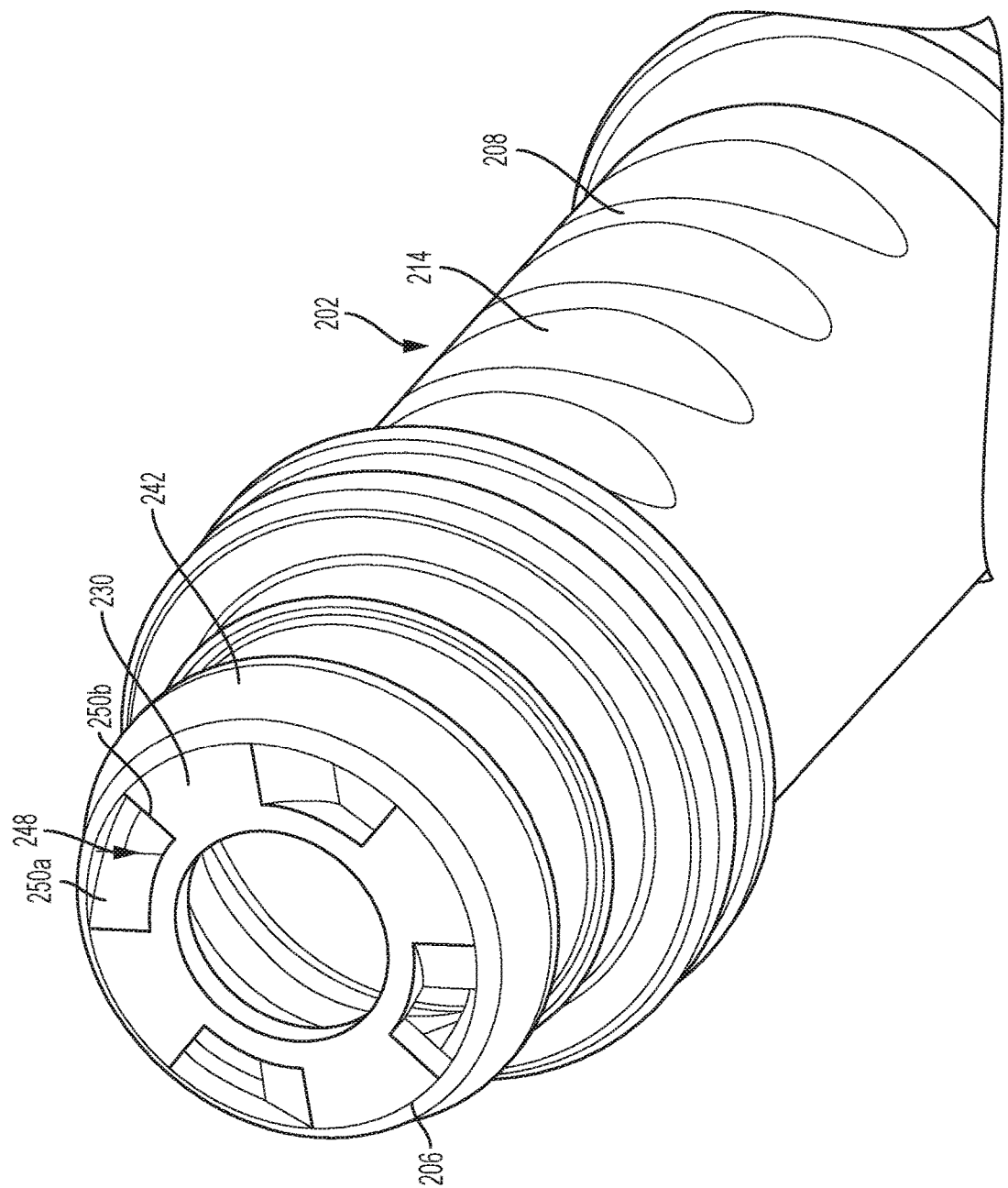
FIG. 28 is an enlarged view of an outer housing of the adapter of FIG. 25.

With reference to FIG. 28, the proximal end 206 of the housing 202 includes a plurality of apertures 248 corresponding to the teeth 244 of the inner member 226. The apertures 248 are defined in the proximal surface of the housing 202 and are configured to receive the teeth 244 of the inner member 226 when the inner member 226 is inserted in the hub cover 228. The apertures 248 are spaced in a circular pattern in the proximal surface of the housing 202. In one aspect, the apertures 248 extend through the entire proximal surface of the housing 202. In another aspect, the apertures 248 only extend through a portion of the proximal surface of the housing 202. In one aspect, four apertures 248 are defined in the proximal surface of the housing 202. Each aperture 248 includes an angled portion 250a and a locking surface 250b. It is also contemplated that corresponding teeth may be used in place of the apertures 248.

After the inner member 226 has been locked in the hub cover 228, the teeth 244 of the inner member 226 and the apertures 248 defined in the housing 202 are configured to interact so as to permit rotation of the inner member 226 within the hub cover 228 in a counterclockwise direction and prevent rotation of the inner member 226 within the hub cover 228 in a clockwise direction. As the inner member 226 is rotated in the counterclockwise direction, the teeth 244 of the inner member 226 continue to slide along the angled portions 250a of the apertures 248 of the housing 202 so that rotation of the inner member 226 is not prevented. Since the inner member 226 can continue to rotate in the counterclockwise direction, any accidental or inadvertent rotation of a fluid line connected to the connector 236 is also prevented. In one example, this accidental or inadvertent rotation of the fluid line may occur when a syringe or IV line is being attached. When the inner member 226 is rotated in the clockwise direction, the locking surface 246b of the teeth 244 of the inner member 226 are held against the locking surfaces 250b of the apertures 248 of the housing 202 so that rotation of the inner member 226 within the hub cover 228 is prevented. Since the inner member 226 is prevented from rotating in the clockwise direction, the inner member 226 remains stationary when a fluid line is being connected to the connector 236 of the inner member 226.

When the user wishes to remove the fluid path line from the connector 236, the user can grip and press the hub cover 228 inwardly against the inner member 226. Since the hub cover 228 is pressed against the inner member 226, the inner member 226 is prevented from rotating in either the clockwise or counterclockwise direction. Since the inner member 226 is held stationary in the counterclockwise direction in particular, the user can rotate the fluid line on the connector 236 in a counterclockwise direction to permit removal of the fluid line from the connector 236. The removal of the fluid line from the connector 236 requires the user to actively grip and press the hub cover 228 against the inner member 226.

Using this configuration, the fluid line cannot inadvertently rotate on the connector 236 to allow for an inadvertent removal of the fluid line from the connector 236.

Figure 30:
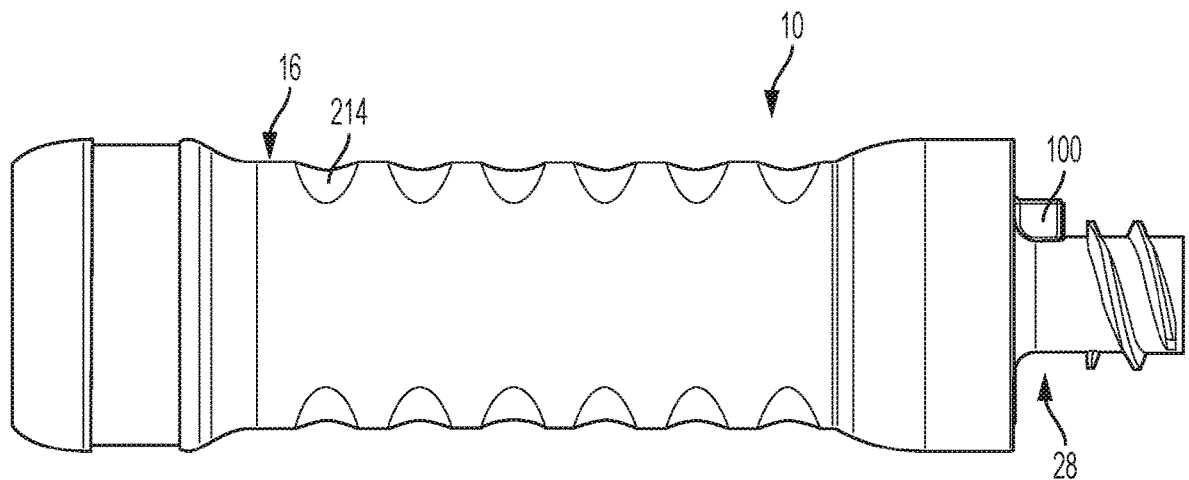
FIG. 30 is a side view of another aspect of the adapter according to the present disclosure.

As shown in FIG. 30, in another aspect of the disclosure the grip indentations 214 provided on the housing 202 of the adapter 200 can also be provided on the housing 16 of the adapter 10 described above. Furthermore, in this aspect, the thumb stop 100 of FIG. 21 can also be used on the inner member 28 of the adapter 10.

Figure 31:
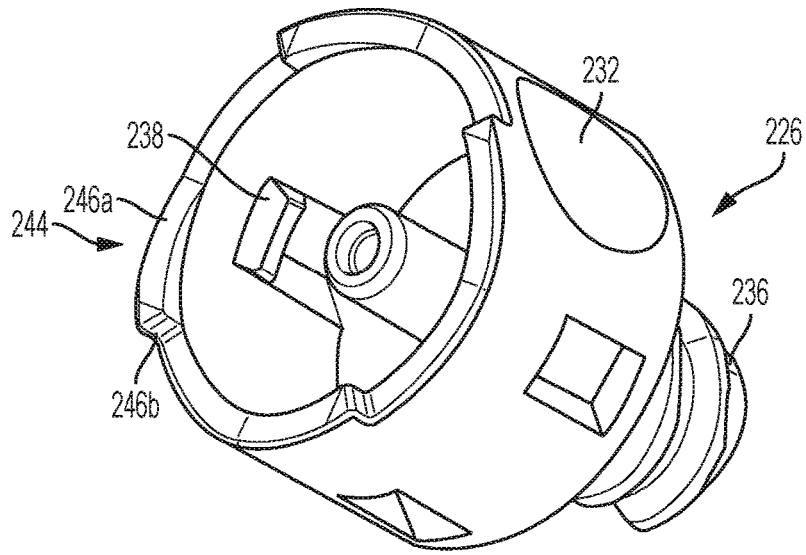
FIG. 31 is a perspective view of an inner member according to another aspect of the present disclosure.
Figure 32:
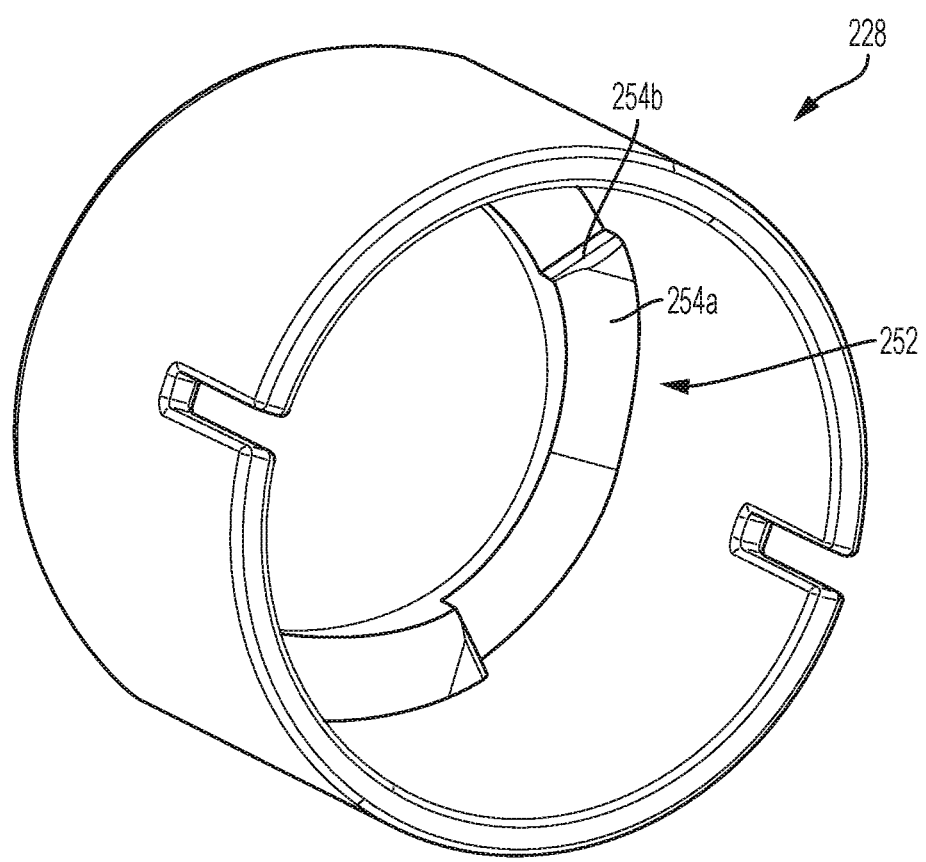
FIG. 32 is a perspective view of a hub cover according to another aspect of the present disclosure.

With reference to FIGS. 31 and 32, another locking arrangement between the inner member 226 and the hub cover 228 of the adapter 200 is described. As shown in FIG. 31, instead of the teeth 244 being provided on a proximal inner surface of the inner member 226, the teeth 244 are provided on a distal end of the inner member 226. The teeth 244 are formed on the distal end of the inner member 226 and include the angled portion 246a and the locking surface 246b. As shown in FIG. 32, corresponding teeth 252 are provided on an inner surface of the hub cover 228 to interact with the teeth 244 of the inner member 226 when the inner member 226 is locked in the hub cover 228. The teeth 244 of the inner member 226 and the teeth 252 of the hub cover 228 interact to provide the same locking features that are provided by the teeth 244 of the inner member 226 and the apertures 248 of the housing 202. The teeth 252 of the hub cover 228 include an angled portion 254a and a locking surface 254b. The locking surfaces 246b, 254b of the inner member 226 and the hub cover 228, respectively, are configured to interact to prevent clockwise rotation of the inner member 226 within the hub cover 228.

Although the invention has been described in detail for the purpose of illustration based on what is currently considered to be the most practical and preferred aspects, it is to be understood that such detail is solely for that purpose and that the invention is not limited to the disclosed aspects, but, on the contrary, is intended to cover modifications and equivalent arrangements that are within the spirit and scope of the appended claims. For example, it is to be understood that the present invention contemplates that, to the extent possible, one or more features of any aspect can be combined with one or more features of any other aspect.

The invention claimed is:

1. An adapter for connection with a fluid container, the adapter comprising:
   an outer housing having a distal end, a proximal end, and a sidewall extending between the distal end and the proximal end, a flange extending from the sidewall, the flange defining a proximal side and a distal side;
   an inner member comprising a rotatable body inserted within the outer housing, a connector extending from the rotatable body configured to connect the adapter to a fluid container, and at least one grasping member extending from the inner member;
   a resilient member, the resilient member inserted within the outer housing and biasing the distal side of the flange;
   a first locking arrangement engageable with the inner member and configured to restrict the inner member from rotating relative to the outer housing in a first direction, the first locking arrangement located proximal to the flange within the outer housing; and
   a second locking arrangement engageable with the inner member and configured to restrict the inner member from moving in a proximal direction relative to the outer housing,
   wherein the adapter is transitionable between a disengaged state, in which both the first locking arrangement and the second locking arrangement are not engaged with the inner member, a first fully engaged state in which the first locking arrangement engages the inner member, and a second fully engaged state in which the second locking arrangement engages the inner member, and
   wherein the second locking member engages with a top surface of the inner member.

2. The adapter according to claim 1, wherein the inner member is rotatable in both the first direction and a second direction when the connector is in the disengaged state, wherein the inner member is prevented from rotating in a first direction when the connector is in the first fully engaged state; and wherein the inner member is prevented from retracting proximally out of the housing while permitting the inner member to rotate freely in the second fully engaged state.

3. The adapter according to claim 1, wherein the inner member is transitionable from an extended position to a recessed position by applying a compressive force to the inner member.

4. The adapter according to claim 1, wherein the first locking arrangement comprises at least one tooth extending inward from an inner surface of the sidewall of the outer housing and a corresponding tooth on the rotatable body of the inner member configured to engage the tooth on the sidewall.

5. The adapter according to claim 4, wherein the at least one tooth extending inward from the inner surface of the sidewall of the outer housing and the corresponding tooth on the rotatable body of the inner member comprise an angled portion and a vertical locking surface.

6. The adapter according to claim 1, wherein the first locking arrangement comprises a plurality of teeth extending around a circumferential inner surface of the sidewall of the outer housing and a plurality of corresponding teeth extending from a distal end of the rotatable body of the inner member.

7. The adapter according to claim 1, wherein the second locking arrangement comprises at least one inwardly extending locking tab connected to a portion of an inner surface of the sidewall of the outer housing and configured to engage the proximal surface of the inner member.

8. The adapter according to claim 7, wherein the second locking arrangement comprises at least two inwardly extending locking tabs positioned on opposing sides of the sidewall of the outer housing.

9. The adapter according to claim 7, wherein the at least one locking tab comprises a locking surface configured such that applying a compressive force to the inner member biases the tab outward to insert the inner member into the outer housing.

10. The adapter according to claim 1, wherein the connector comprises an outer surface with helical threads, configured to engage corresponding threads on an inner surface of a portion of the fluid container.

11. The adapter according to claim 10, wherein the connector comprises a luer connector configured to receive a corresponding luer connector of the fluid container.

12. The adapter according to claim 1,
   wherein the at least one grasping member comprises two curved flanges extending from a proximal surface of the inner member, each curved flange including a planar portion and an angled portion extending from each end of the planar portion, and wherein the curved flanges are configured for grasping by the user to prevent rotation of the inner member in a second direction, in which the second direction is opposite the first direction.

13. The adapter according to claim 1,
wherein the at least one grasping member comprises two bumps extending from a proximal surface of the inner member, each bump having a substantially hemispherical shape, and
wherein the bumps are configured for pressing by the user to prevent rotation of the inner member in a second direction, in which the second direction is opposite the first direction.

14. The adapter according to claim 1,
wherein the at least one grasping member comprises two flanges positioned on the connector, each flange comprising a vertical portion that extends vertically along a side surface of the connector, and
wherein the flanges are configured for grasping by the user to prevent rotation of the inner member in a second direction, in which the second direction is opposite the first direction.

15. The adapter according to claim 14, wherein one of the flanges further comprises a horizontal portion that extends horizontally from the connector and perpendicular to the vertical portion.

16. The adapter according to claim 1,
wherein the at least one grasping member comprises a thumb stop extending horizontally from the connector and vertically from the body, and
wherein the thumb stop is configured for grasping by the user to prevent rotation of the inner member in a second direction, in which the second direction is opposite the first direction.

17. The adapter according to claim 1,
wherein the at least one grasping member comprises a groove defined in the body of the inner member, and
wherein the groove is configured for grasping by the user to prevent rotation of the inner member in a second direction, in which the second direction is opposite the first direction.

18. A method of disconnecting a fluid container to an adapter comprising:
providing an adapter comprising:
an outer housing having a distal end, a proximal end, and a substantially cylindrical sidewall extending between the distal end and the proximal end, a flange extending from the sidewall, the flange defining a proximal side and a distal side;
a resilient member, the resilient member inserted within the outer housing and biasing the distal side of the flange;
an inner member comprising a body rotatably inserted within the outer housing, a connector extending from the body configured to connect the adapter to a fluid container, and at least one grasping member extending from the inner member, the grasping member being configured for grasping by a user of the adapter;
a first locking arrangement engageable with the inner member and configured to restrict the inner member from rotating relative to the outer housing in a first direction, the first locking arrangement located proximal to the flange within the outer housing; and
a second locking arrangement engageable with a proximal surface of the inner member and configured to restrict the inner member from moving in a proximal direction relative to the outer housing, wherein the second locking arrangement engages with a top surface of the inner member;
grasping the at least one grasping member;
moving the fluid container in an axial direction towards the adapter; and
rotating the fluid container to disconnect the fluid container from the inner member of the adapter.

19. The method according to claim 18,
wherein the at least one grasping member comprises two curved flanges extending from a proximal surface of the inner member, each curved flange including a planar portion and an angled portion extending from each end of the planar portion, and
wherein the curved flanges are configured for grasping by the user to prevent rotation of the inner member in a second direction, in which the second direction is opposite the first direction.

20. The method according to claim 18,
wherein the at least one grasping member comprises two flanges positioned on the connector, each flange comprising a vertical portion that extends vertically along a side surface of the connector, and
wherein the flanges are configured for grasping by the user to prevent rotation of the inner member in a second direction, in which the second direction is opposite the first direction.

21. An adapter for connection with a fluid container, the adapter comprising:
an outer housing having a distal end, a proximal end, and a sidewall extending between the distal end and the proximal end, a flange extending from the sidewall;
a resilient member, the resilient member inserted within the outer housing and biasing the flange;
a hub cover attached to the proximal end of the outer housing;
an inner member comprising a rotatable body inserted within the outer housing and a connector extending from the rotatable body configured to connect the adapter to a fluid container;
a first locking arrangement engageable with the outer housing and configured to restrict the inner member from rotating relative to the outer housing in a first direction; and
a second locking arrangement engageable with the outer housing and configured to restrict the inner member from moving in a proximal direction relative to the outer housing,
wherein the adapter is transitionable between a disengaged state, in which both the first locking arrangement and the second locking arrangement are not engaged with the inner member, a first fully engaged state in which the first locking arrangement engages the outer housing, and a second fully engaged state in which the second locking arrangement engages the outer housing,
wherein the second locking arrangement engages with a top surface of the inner member, and
wherein the first locking arrangement comprises at least one tooth extending inward from an inner surface of the inner member and at least one recess defined in the proximal end of the outer housing configured to engage the tooth on the inner member.

22. The adapter according to claim 21, wherein the hub cover is integrally formed on the proximal end of the outer housing and is configured to surround the rotatable body of the inner member when the inner member is connected to the outer housing.

23. The adapter according to claim 21, wherein the hub cover is substantially flexible so as to contact the inner member to prevent rotation of the inner member relative to the outer housing.

24. The adapter according to claim 21, wherein the inner member is rotatable in both the first direction and a second direction when the connector is in the disengaged state, wherein the inner member is prevented from rotating in a first direction when the connector is in the first fully engaged state; and wherein the inner member is prevented from retracting proximally out of the housing while permitting the inner member to rotate freely in the second fully engaged state.

25. The adapter according to claim 21, wherein the inner member is transitionable from an extended position to a recessed position by applying a compressive force to the inner member.

26. The adapter according to claim 21, wherein the at least one tooth extending inward from the inner member and the corresponding recess defined in the outer housing comprise an angled portion and a vertical locking surface.

27. The adapter according to claim 21, wherein the second locking arrangement comprises at least one inwardly extending locking tab connected to a portion of an inner surface of the inner member and configured to engage a locking protrusion extending from the proximal end of the outer housing.

28. The adapter according to claim 27, wherein the at least one locking tab comprises a locking surface configured such that applying a compressive force to the inner member biases the locking tab outward to insert the inner member into the outer housing.

29. The adapter according to claim 21, wherein the sidewall of the outer housing defines at least one indentation to assist a user in gripping the adapter.

* * * * *